(12) United States Patent
Madhani

(10) Patent No.: US 8,052,185 B2
(45) Date of Patent: Nov. 8, 2011

(54) ROBOT HAND WITH HUMANOID FINGERS

(75) Inventor: Akhil J. Madhani, Pasadena, CA (US)

(73) Assignee: Disney Enterprises, Inc., Burbank, CA (US)

( * ) Notice: Subject to any disclaimer, the term of this patent is extended or adjusted under 35 U.S.C. 154(b) by 337 days.

(21) Appl. No.: 12/421,413

(22) Filed: Apr. 9, 2009

(65) Prior Publication Data
US 2010/0259057 A1    Oct. 14, 2010

(51) Int. Cl.
B66C 1/42    (2006.01)
(52) U.S. Cl. ............... 294/106; 294/111; 901/21; 414/7
(58) Field of Classification Search ................ 294/106, 294/111; 901/21, 30, 31; 414/2, 3, 4, 5, 414/7; 623/21.15–21.17, 21.19
See application file for complete search history.

(56) References Cited

U.S. PATENT DOCUMENTS

| | | | |
|---|---|---|---|
| 4,402,053 A | 8/1983 | Kelley et al. | |
| 4,555,960 A | 12/1985 | King | |
| 4,661,032 A | 4/1987 | Arai | |
| 4,795,296 A | 1/1989 | Jau | |
| 4,834,761 A | 5/1989 | Walters | |
| 4,865,376 A * | 9/1989 | Leaver et al. | 294/111 |
| 4,913,000 A | 4/1990 | Wyllie | |
| 4,914,976 A | 4/1990 | Wyllie | |
| 4,921,293 A * | 5/1990 | Ruoff et al. | 294/111 |
| 4,946,380 A * | 8/1990 | Lee | 623/24 |
| 4,955,918 A * | 9/1990 | Lee | 623/24 |
| 4,976,191 A | 12/1990 | Suzumori et al. | |
| 5,007,300 A | 4/1991 | Siva | |
| 5,038,089 A | 8/1991 | Szakaly | |
| 5,095,303 A | 3/1992 | Clark et al. | |
| 5,132,672 A | 7/1992 | Clark | |
| 5,142,931 A | 9/1992 | Menahem | |

(Continued)

FOREIGN PATENT DOCUMENTS
EP    1195151 A1    10/2002

OTHER PUBLICATIONS www.shadowrobot.com, Shadow Robot Company Ltd., London, UK, retrieved Apr. 13, 2009.

(Continued)

Primary Examiner — Saul Rodriguez
Assistant Examiner — Stephen Vu
(74) Attorney, Agent, or Firm — Marsh Fischmann & Breyfogle LLP; Kent A. Lembke

(57) ABSTRACT

A robotic hand with finger assemblies to better simulate human hand form factors and gestures. For each finger assembly, the robotic hand includes a finger drive assembly that is operable to selectively apply tension to four elongated and flexible tension elements (e.g., steel cable). Each of the finger assemblies includes a set of links or link members that are actuated or moved by the selective tensioning/movement of the tension elements by the drive assembly. The links are interconnected with pivotal joints such that they have three degrees-of-freedom, and the finger assembly includes a set of pulleys that are supported on the links and that are arranged to provide support and to guide the tension elements through the finger assembly. The tension elements preferably extend only partially about any one of the pulleys, whereby the finger assembly utilizes "n+1" actuation with non-helical wrapping of the tension elements.

34 Claims, 18 Drawing Sheets

U.S. PATENT DOCUMENTS

| | | | |
|---|---|---|---|
| 5,157,315 | A | 10/1992 | Miyake et al. |
| 5,182,961 | A | 2/1993 | Menahem et al. |
| 5,223,776 | A | 6/1993 | Radke et al. |
| 5,263,382 | A | 11/1993 | Brooks et al. |
| 5,271,290 | A | 12/1993 | Fischer |
| 5,305,777 | A | 4/1994 | Nakamura et al. |
| 5,313,230 | A | 5/1994 | Venolia et al. |
| 5,451,134 | A | 9/1995 | Bryfogle |
| 5,565,891 | A | 10/1996 | Armstrong |
| 5,589,828 | A | 12/1996 | Armstrong |
| 5,737,500 | A | 4/1998 | Seraji et al. |
| 5,792,135 | A | 8/1998 | Madhani et al. |
| 5,808,665 | A | 9/1998 | Green |
| 5,816,105 | A | 10/1998 | Adelstein |
| 6,244,644 | B1 * | 6/2001 | Lovchik et al. ............... 294/111 |
| 6,663,465 | B2 | 12/2003 | Gross |
| 6,668,678 | B1 | 12/2003 | Baba et al. |
| 6,905,491 | B1 | 6/2005 | Wang et al. |
| 7,155,316 | B2 | 12/2006 | Sutherland et al. |
| 7,168,748 | B2 | 1/2007 | Townsend et al. |
| 7,296,835 | B2 * | 11/2007 | Blackwell et al. ............ 294/111 |
| 7,410,338 | B2 | 8/2008 | Schiele et al. |

OTHER PUBLICATIONS

European search report for EP Application No. 10159530.4, dated Jul. 23, 2010, Munich, Germany, Applicant Disney Enterprises, Inc., Reference No. 323948EP/DJW.

* cited by examiner

ROBOT HAND WITH HUMANOID FINGERS

BACKGROUND OF THE INVENTION

1. Field of the Invention

The present invention generally relates to robotics and, more particularly, to a robot hand that includes fingers designed to fit within a human form factor and to move and behave more like fingers of a human hand.

2. Relevant Background

In recent years, there has been an increasing demand for robots that more closely simulate or mimic humans. For example, animatronic figures are robotic systems that are designed to duplicate characters as closely possible, and many of these characters are human or human-like characters. Robots used to provide animatronic figures may be displayed as part of rides, attractions, theater shows, retail displays, and other entertainment venues. In these settings, there is desire for the animatronic figures or robots to mimic the character, such as a character from a movie or animated film, in terms of their shape, dexterity, and ability to produce motions and forces (e.g., dynamics of a mimicked character). In addition, it may be useful for a robot to be designed to reproduce physical abilities such as walking and manipulating objects such as with fingers of a robotic hand. Many characters are made to have human characteristics or features such as hands, fingers, and the like, even when they are not a human or human-like, e.g., ants, birds, monsters, and so on with human-like hands and fingers.

Increasingly, robot designers and manufacturers are being requested to design robotic systems with human-like or anthropomorphized features and capabilities to be used in non-entertainment applications. These uses may include a robot designed for patient care in a hospital or physical therapy setting, home care for a patient, or a robot for performing household tasks. In these applications, robotic systems are expected to interact with humans in a useful manner but also in an appealing manner. Robots are generally found more appealing when they look and behave in a manner familiar to humans, and it has generally been accepted that an effective human-robot interaction is provided by a human-like robotic system or a robot with human characteristics or features such as hands and fingers.

In entertainment and other applications, a challenging and important aspect is the design of the hands of the robot. For example, the hands of a robotic character, even if the character does not have human hands, are typically designed in an attempt to mimic the form, dexterity, dynamics, and functionality of human hands. Unfortunately, none of the existing robotic hand designs have successfully met all the design challenges in presenting a robotic human hand. There are numerous end-effector designs in existence, but these are generally variations of simplistic two-fingered grippers or jaws with a single degree-of-freedom that are used to grasp or clamp objects.

Several robotic "hands" have been produced, but some of these designs only bear a greater resemblance to human hands than the two-clawed gripper but typically are lacking in terms of dexterity and form. For example, a human finger has four degrees-of-freedom (DOF) (although only 3 DOF are typically controlled independently). However, robotic hands typically have much fewer DOF with some hands only providing one DOF per band, which significantly limits their dexterity and motion capability. Some will provide one DOF per finger such that each finger can be articulated independently. However, the finger motion may be a simplistic motion such as curling upon itself with no side-to-side motion of each finger or independent movement of parts or digits of the fingers as found in a human hand.

Existing robot hands that provide increased numbers of DOF often are very complex or fail to match a human form factor. For example, one existing hand design provides 24 DOF total for the hand with relatively good finger form factor compliance, but this hand design requires the number of cables (or "tendons") and actuators to be up to twice the number of DOF or forty-eight in this case. This results in a large form factor at the wrist and forearm that is less human in appearance. An additional problem with this hand design is that the cables or tendons used to actuate the finger movements run over fixed, un-lubricated metal or plastic runners creating significant friction and wear issues.

Another hand provides two digits for each "finger" and utilizes a pulley and actuator mechanism that does not lend itself to being packaged with human form factor (e.g., thin elongated fingers, a relatively small wrist, and thin palm). Particularly, in this hand design, an "n+1" arrangement is used for the drive cables or tendons, which reduces the number of cables required, but the pulley arrangement is such that the cables each wrap about their supporting pulleys by more than 360 degrees, which requires that the pulleys be thick (e.g., generally twice the cable thickness) making it difficult to place in a finger form factor packaging. Also, the cables create additional friction and wear as they cross over one another and rub upon each other during operation of the hand. Further, this robot hand requires four motor drives per finger, which increases costs, complexity, form factor, and maintenance.

Yet other robotic hands may be designed to use a thicker cable and actuate the fingers with a push/pull arrangement. Motors are proximally mounted to the wrist that is used to support the hand. To transmit power through the wrist, flexible drive shafts are used, with rotary motion as opposed to linear motion being transmitted through the wrist. This rotary motion is converted to linear motion by means of lead screws mounted in the palm of the hand. This provides the advantage of passing a number of drive shafts equal to the number of DOF of the hand (e.g., twelve in one example of this design). However, one disadvantage of the rotary drive hand is that twelve lead screws must be packaged within the palm of the hand, resulting in a large (i.e., greater than human-sized) palm. Also, the use of a thick cable in a push/pull arrangement to actuate the finger DOF limits the amount of force that may be applied in the "push" direction, which may limit the uses of this robotic hand design.

Hence, there remains a need for hand design for a robot or robotic system that meets the challenges associated with a human form factor while achieving the functionality expected of a human hand. It is preferable that such a hand design would include fingers with a similar number of digits as found in a human hand and with dexterity and movement that is more human like (e.g., fingers that move with a similar number of DOF). It is also preferable that the robot hand design includes a relatively small number of components and addresses wear and maintenance issues associated with use of actuating cables (or tendons).

SUMMARY OF THE INVENTION

The present invention addresses the above problems by providing a design for a robot hand with fingers with three digits and human-like form and movement to provide a number of advantages over prior hand and/or finger designs. Embodiments of the robot hands described herein address factors including the ability to fit a human form factor, a desirable DOF (e.g., three DOF per finger provided on or supported within the robot hand), method of actuation, the ability to precisely control the joints, the ability to apply sufficient forces to grasp objects, and longevity (e.g., reduce tendon or cable friction and other wear that may otherwise cause early failure or force added maintenance).

As will become clear, some embodiments of the described robot hands use the minimum practical number of tension elements (e.g., cables, tendons, or the like) to actuate three DOF fingers (e.g., n+1 actuation using four cables or tension elements). This is a significant advantage when routing the cable or tendons through a two-jointed, flexible wrist, which provides a very constrained space when limited to a form factor of a human wrist. The robot hands of some embodiments may use a reduced or even a minimum number of motors to actuate the fingers. Motors have associated complexity, cost, and packaging constraints, and, hence, reducing the number of actuators or drive motors leads to a more desirable hand design. Additionally, hand embodiments use a pulley design that allows the finger design to fit within a human form factor. Many prior hand designs were not forced to comply with a human form factor constraint, but such a constraint is called for in many animatronic and non-entertainment robot applications. Further, the use of pulleys in the fingers themselves (e.g., pulleys supported upon finger digits or segments of each finger assembly of a hand), instead of sliding cables over or through un-lubricated elements, significantly reduces friction and decreases wear (i.e., increases longevity). Hand embodiments may use a passive tendon tension maintenance system to provide pre-tensioning of the finger drive or actuating cables/tendons. This is in contrast to an active approach that requires the use of additional motors along with their associated hardware, electronic and software complexity, and added cost. Yet further, embodiments of the robot hand described herein typically use fixed kinematic relationships between the actuator motion and finger joint motion.

More particularly, a robotic hand is provided with at least one finger assembly and, more typically, five finger assemblies may be included to better simulate a human hand. For each finger assembly, the robotic hand includes a finger drive assembly that is operable to selectively apply tension to four elongated and flexible tension elements (e.g., steel cable or the like). Each of the finger assemblies includes a set of links or link members that are actuated or moved by the selective tensioning/movement of the tension elements by the drive assembly. The links are interconnected with pivotal joints such that they have 3 DOF, and the finger assembly includes a set of pulleys that are supported on the links and that are arranged to provide support and to guide the tension elements through the finger assembly. The tension elements preferably extend only partially about any one of the pulleys (e.g., only a partial wrapping about each contacted pulley), whereby the finger assembly utilizes "n+1" actuation (where "n" is the DOF and the value is the number of tension elements) with non-helical wrapping of the tension elements.

In some cases, the pulleys may be about half the height of pulleys used in devices using helical wrapping. In helical wrapping systems, a pulley without any grooves or one wide, flat groove may be used so that a helix can form while in other applications a single, helically machined groove is used. In either case, the use of helical wrapping requires additional room for the cable wrap to "walk" across the face of the pulley. In contrast within some embodiments described herein, each of the cables or tension elements may wrap around less than half of the circumference of each contacted pulley, with some contacting on about a quarter wrap or 90 degrees. The set of links may include first, second, and third digits or digit links (e.g., to simulate the three digits or segments of a human finger). In such cases, the third digit link may be pivotally mounted to the second digit link, which in turn is pivotally connected to the first digit link. The first and second digit links may be independently actuated or operable by the drive assembly, with a pair of the tension elements or cables terminating on each of these two links. An additional coupler link may be included in the finger assembly to interconnect the third digit link to the second digit link such that the third digit link is actuated by movement of the second digit link (e.g., the third digit link may be passively actuated to behave as a follower or slave link to the second digit link).

The hand may also include a palm element or plate, a base link member, and a first digit mounting link member. The base link member is rigidly attached to the palm plate to support the finger assembly within the hand. The first digit mounting link member is pivotally mounted to the base link member for pivoting about a first axis (such as with a range of motion of about 40 degrees or 20 degrees or less in each rotation direction) while the first digit link is pivotally coupled to the first digit mounting link member for pivoting about a second axis that is transverse or even orthogonal to the first axis (such as with a range of less than about 15 degrees in a counterclockwise direction away from the palm plate and in the range of about 75 to 100 degrees in a clockwise direction toward the palm plate). In this manner, the range of motion of the first digit of the finger assembly is similar to a human finger with a side-to-side movement (e.g., plus or minus 13 degrees or the like relative to a vertical plane passing through the first axis) and with a small backward bending (such as less that about 15 degrees relative to a horizontal plane passing through second axis) but a large forward bending movement (such as more than 90 degrees). The third digit link is actuated by the second digit link such that it and the second digit link straighten with the backward bending similar to a human finger and it and the second digit link curl further inward with the forward bending or curling of the first digit link (such as for forming a fist or grasping an object). In some embodiments, the drive assembly is adapted to provide a passive tension maintenance system to maintain a desired tension on the four tension elements, and this and other features allow three actuators (e.g., drive motors) to actuate or drive the four tension elements rather than using at least four actuators.

BRIEF DESCRIPTION OF THE DRAWINGS

FIG. 15 illustrates schematically a passive tension maintenance mechanism as may be provided/incorporated within the robotic hand systems such as the system of FIG. 1 or the like;

DETAILED DESCRIPTION OF THE PREFERRED EMBODIMENTS

Briefly, embodiments of the present invention are directed to robotic hand systems that address the longstanding demand to have improved performance with enhanced simulation of a human hand and human fingers. Prior robotic hands either had less joints and digits/segments than found in a human finger (i.e., three segments or digits) or were sized and/or designed such that the fingers, palm, wrist, or other portions would not fit or suit within human form factors. The robotic hand systems described herein provide a hand or hand assembly with fifteen degrees of freedom (DOF) (e.g., three DOF per finger) such that the hand and each finger can create a wide variety of gestures while still fitting within a human form factor. In each finger or finger assembly, a combination of tension elements (e.g., tendons or drive cables that may take the form of flexible steel cables or wires/wire ropes), linkages, and pulleys to actuate four joints per finger, which provides three DOF per finger, while remaining within human size constraints. The actuation uses "n+1" tension elements or tendons such that four tension elements are used to actuate three DOF in each finger. In this manner, each finger takes the form factor of a human finger in part due to the unique pulley and tension element/drive arrangement, and each finger is independently actuated with human-like dexterity, gestures, and ranges of movement of the three digits or segments of the fingers of the robotic hand.

Figure 1:
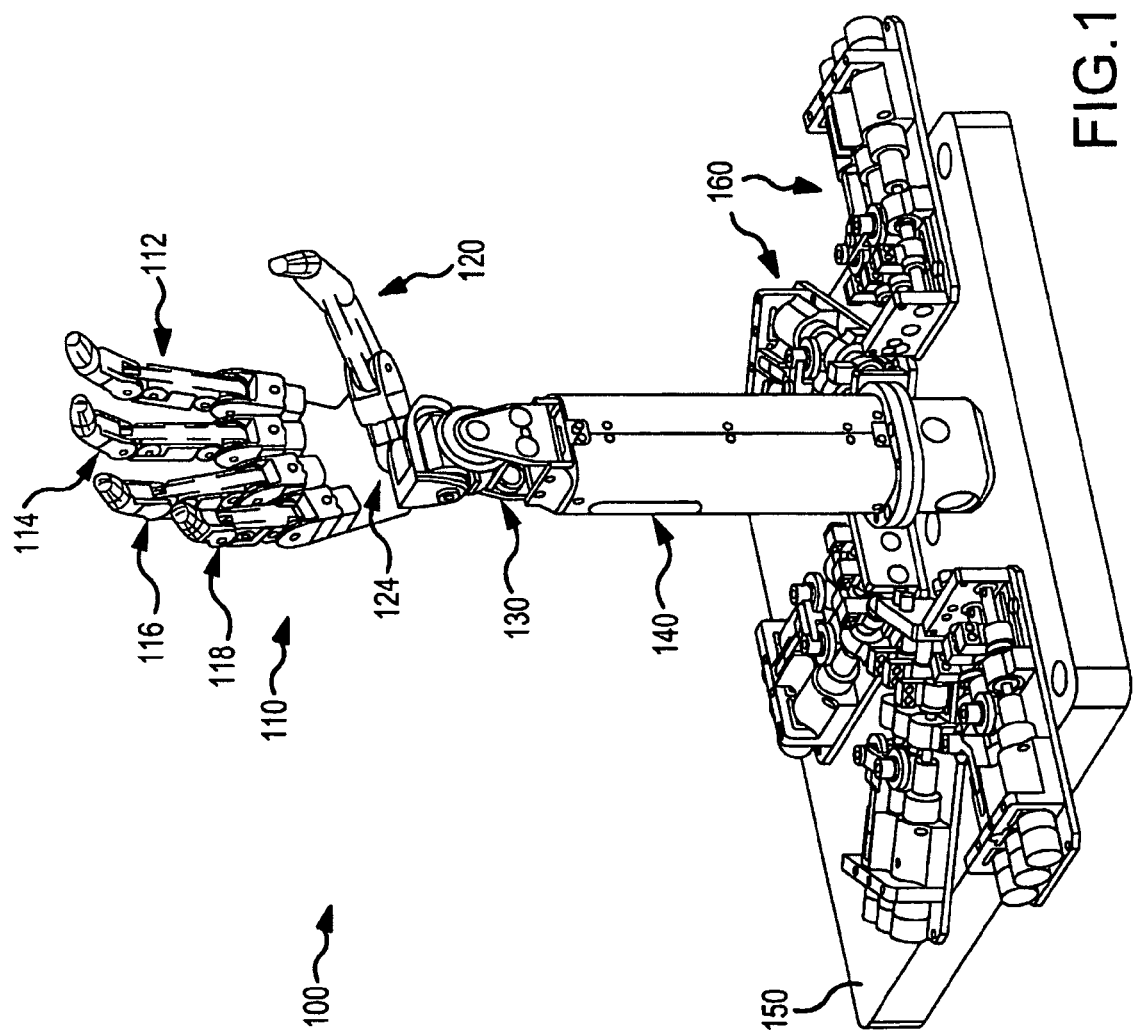
FIG. 1 illustrates a robotic system including a robotic hand or hand assembly, a wrist, a forearm, and drive assemblies or mechanisms for each finger of the robotic hand (i.e., five fingers and five drive assemblies in this example)

FIG. 1 illustrates a robotic hand system 100 in accordance with an embodiment of the invention shown in prototype arrangement (rather than with its motors or drivers sized and positioned into a human form factor arm, shoulder, or body). As shown, the system 100 includes a robotic hand or robotic hand assembly 110, a wrist 130, a forearm 140, and a set of finger drive assemblies or mechanisms 160. The drive assemblies (or motor drives) 160 are mounted on a support base or plate 150, but, in practice, the drive assemblies 160 may be mounted on the forearm 140, on an upper arm (not shown), or in/on the torso (not shown) of the robotic system 100. Although not shown, a number of drive cables or tendons (also called tension elements) would be run from the drive assemblies 160 through the forearm 140 and wrist 130 for connection to portions of the hand assembly 110 (e.g., to independently actuate or drive the fingers of the hand 110).

Components of the system 100 are described in more detail below, but, briefly, it can be seen that the hand assembly 110, which is shown in more detail in FIG. 2, includes five fingers or finger assemblies 112, 114, 116, 118, 120. The finger assemblies 112, 114, 116, 118, 120 are rigidly affixed to a plate 124, which in turn is mounted to the wrist 130 to move with the wrist 130 and forearm 140. The finger assemblies 112, 114, 116, 118, 120 are affixed at a base or initial link member (e.g., link $l_0$ in the following figures) with the next link member (e.g., link $l_1$ in the following figures) attached to the base or initial link member. The plate 124 may be configured to simulate a human palm such as with one of the finger assemblies 120 (e.g., the thumb) mounted out of plane relative to the other four finger assemblies 112, 114, 116, 118, which may be arranged in a semi-circle or other pattern (e.g., with their base link members not arranged perfectly parallel, for example) to, again, better match the arrangement of a human hand and facilitate a desired range of side-to-side and other motion of the finger assemblies 112, 114, 116, 118, and 120. One drive assembly 160 is provided to independently (which may include concurrent operation, too) operate or actuate a paired or corresponding one of the fingers 112, 114, 116, 118, or 120. Hence, in this 5-finger system 100, five drive assemblies 160 are provided to drive the five fingers 112, 114, 116, 118, 120 of the hand assembly 110.

Figure 2:
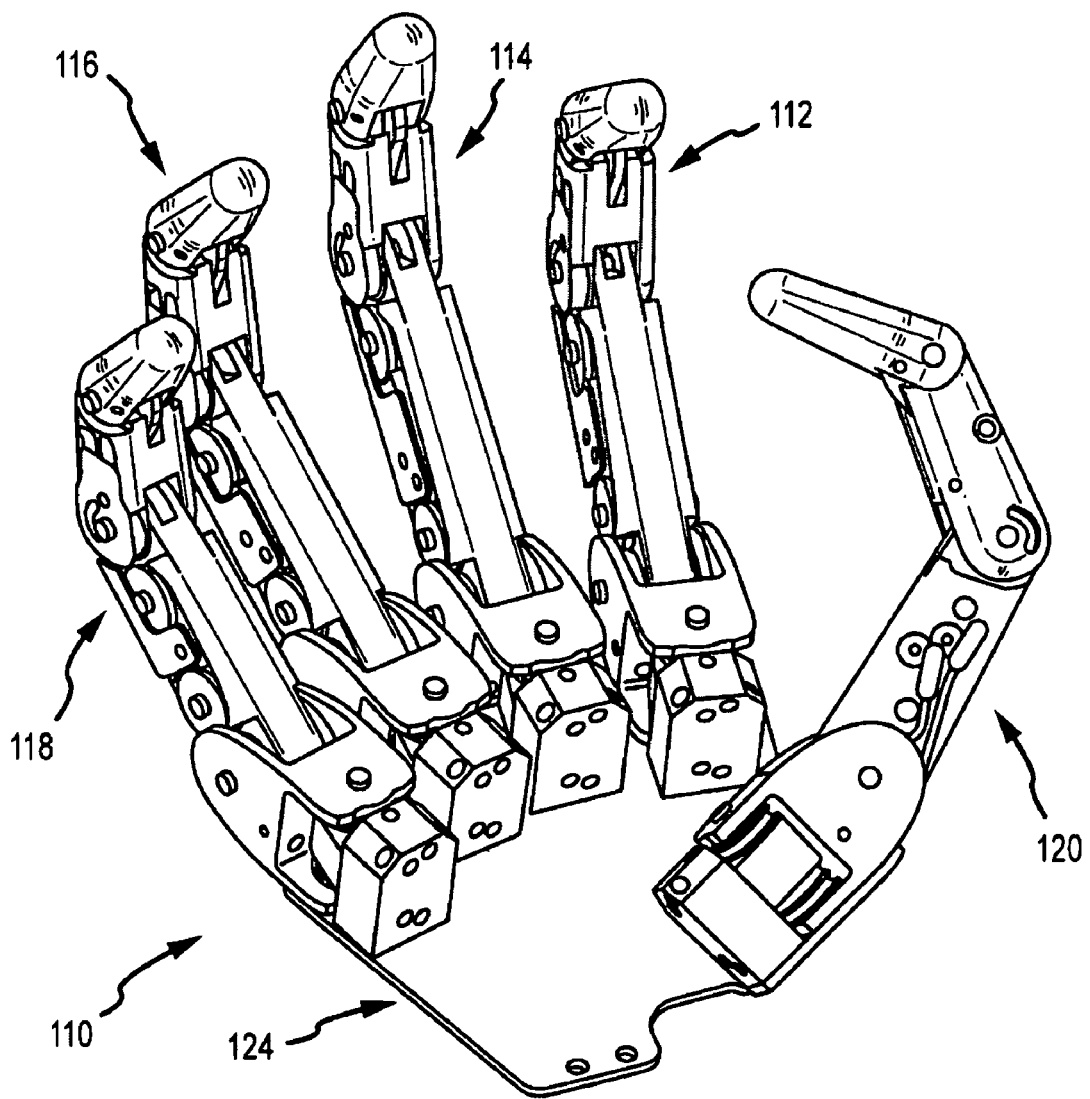
FIG. 2 illustrates an enlarged or more detailed perspective view of the robotic hand of the system of FIG. 1 showing components of the robotic fingers or finger assemblies and their mounting to a supportive plate that, in turn, is attached to the wrist shown in FIG. 1.

The following provides a description of the design of a single one of the finger assemblies 112, 114, 116, 118, or 120 along with its associated drive assembly or motor drive mechanism 160, and such teaching may be applied to any of the drive/finger pairings shown in the system 100 of FIGS. 1 and 2 to provide a more human-like robotic hand system 100. Additionally, the system 100 would include one or more power supplies for powering the drive motors of assemblies 160, and the assemblies 160 would be operated by one or more controllers to selectively operate and actuate the fingers 112, 114, 116, 118, 120 as well as the wrist 130 and other portions of the system 100. Such power and control devices may take many forms to practice the invention, are well known by those skilled in the art, and are not considered limiting to the invention. The number of drive motors (e.g., three per finger), pre-tensioning of the tendons/drive cables, and other features are considered more significant to the present invention and are discussed in detail below.

Figure 3:
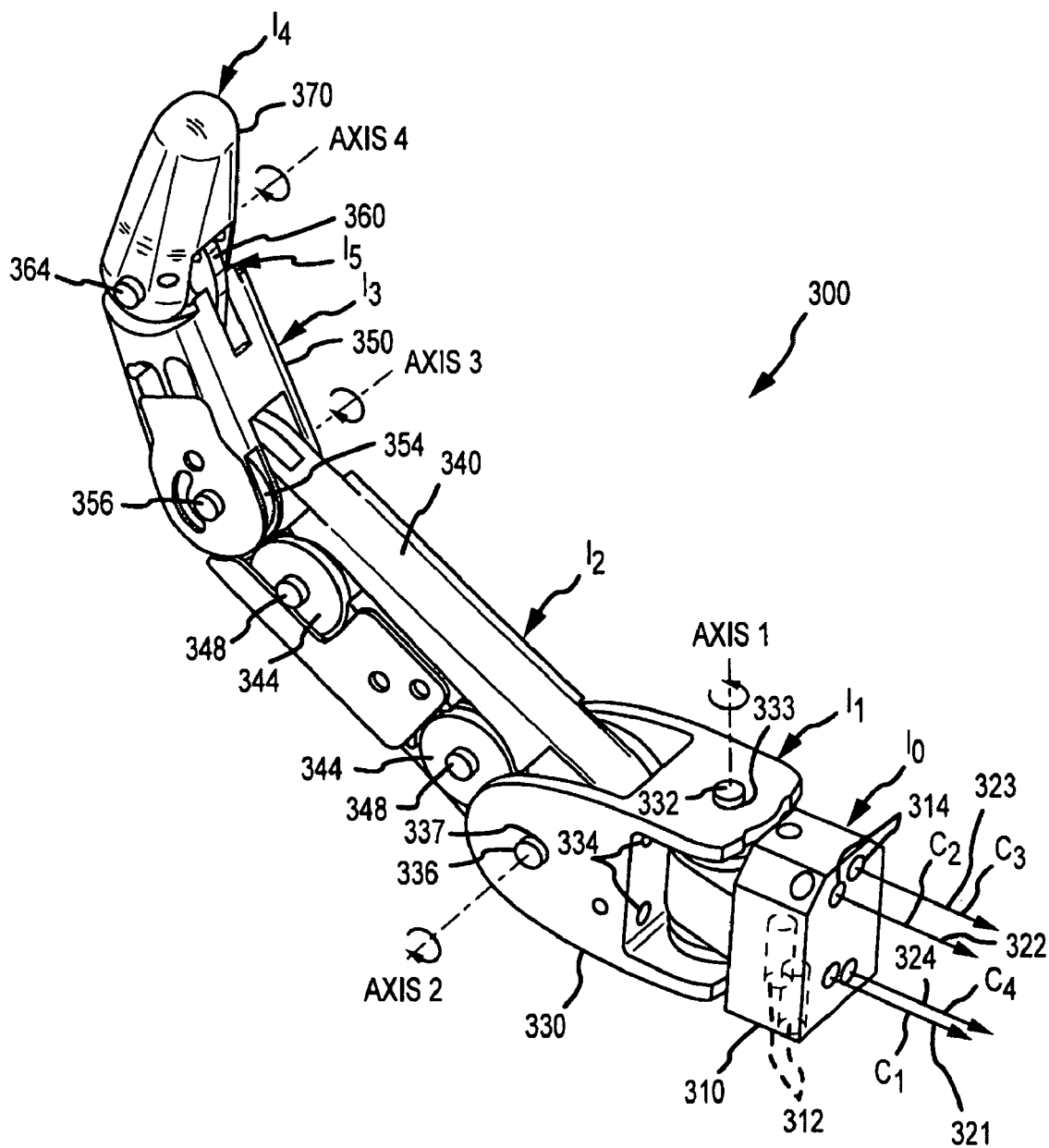
FIG. 3 is a perspective view of a robotic finger or finger assembly in accordance with an embodiment of the invention such as may be used in the hand of FIGS. 1 and 2.

FIG. 3 illustrates a finger assembly 300 such as may be used in a robotic hand of an embodiment of the invention (such as the hand 110 of system 100 of FIGS. 1 and 2). Generally, the finger assembly 300 is made up of a set of six links (labeled $l_0$ to $l_6$ in the figures) and eight shafts (or pivot pins/axles labels $s_0$ to $s_8$ in the figures often with a pivot axis drawn through or along the longitudinal axis of such shafts). In addition, there are nine pulleys (labeled $p_1$ to $p_9$ in the figures) that are mounted in the links or link members and are used to support tendons or tension elements (e.g., steel drive cables or the like), which are used to actuate the finger 300 during use including movement of the three digits with 3 DOF.

As shown in FIG. 3, the finger assembly 300 includes a base or initial link member (with link being used interchangeably with link member) 310 that would be mounted via mounting holes 312, which may take the form of threaded holes, press fit receptacles, or the like, to a hand plate. The base link (i.e., link $l_0$) 310 includes four cable guide channels or passageways 314, and the assembly 300 is shown schematically to be actuated or driven with four cables 321, 322, 323, 324 (shown as $c_1$ to $c_4$ in figures, too) that would extend through the passageways 314 to the next link member 330 (link $l_1$) and its channels or passageways 334. The link member 330 is pivotally mounted to the base link 310 via shaft or pin 332 that extends through hole 333 in link member 330 (and four pulleys as discussed with reference to FIG. 4). The link member 330 (link $l_1$) and its pivotal mounting or joint with base link 310 simulates, in part, functionality of the knuckle of a human hand with side-to-side pivoting or motion about shaft 332 (or Axis 1).

The finger assembly 300 further includes an elongated link member (link $l_2$) 340 mimicking the first digit of a human finger. The link member 340 is pivotally mounted to the link member 330 at a first end via shaft 336 that extends through the link member 340 and a pair of holes 337 in the body of link member 330, which is arranged to extend about both sides of the end of link member 340. The link member (link $l_2$) 340 pivots when actuated by tension elements about shaft 336 (Axis 2). The link member 340 supports a set of pulleys 344 that pivot on the body of link member 340 about mounting/supporting shafts 348 (e.g., the set of pulleys 344 may include four pulleys as shown in the exploded view of FIG. 4 for guiding and supporting the tensioning elements used to actuate the finger assembly 300).

Figure 4:
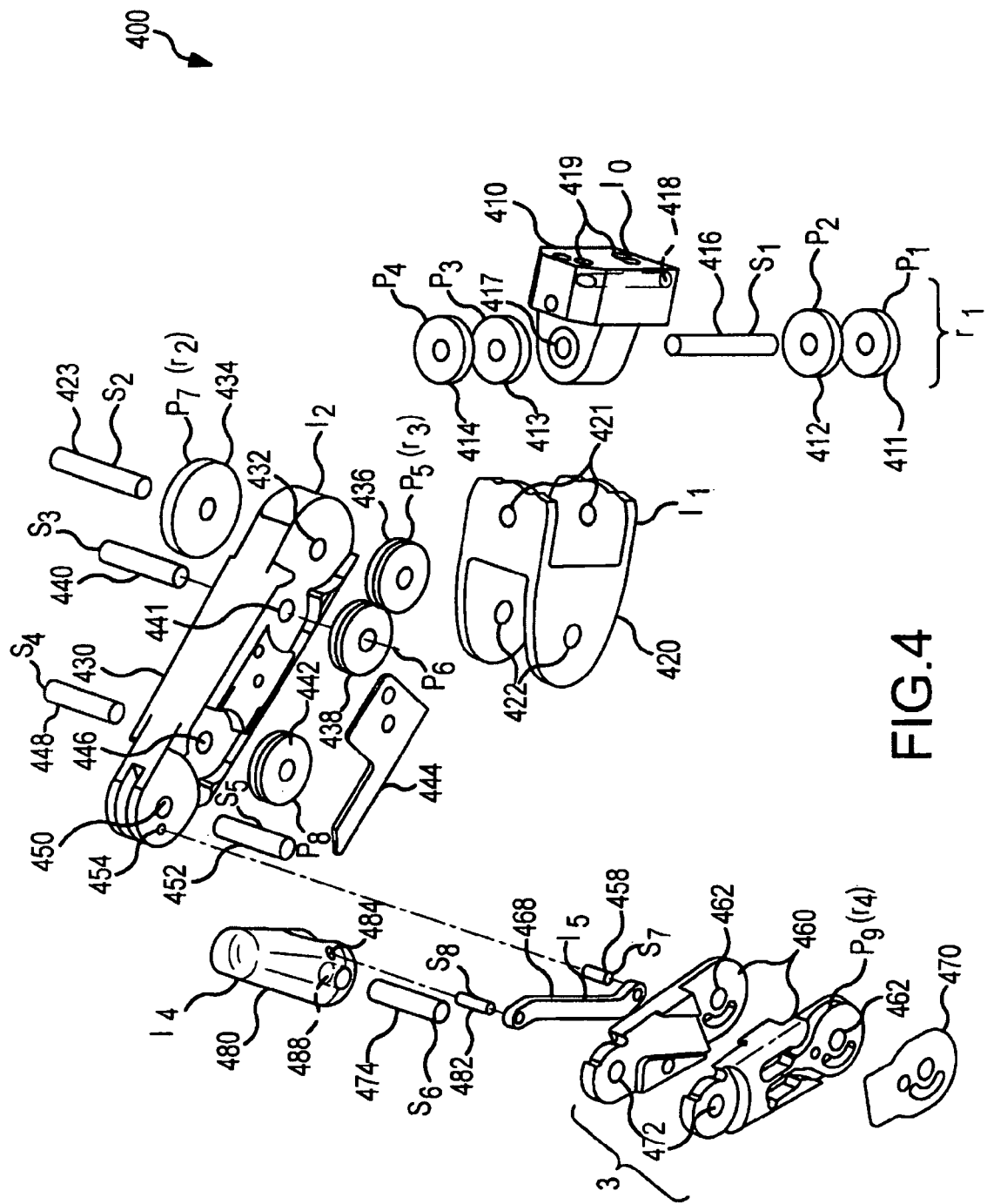
FIG. 4 illustrates an exploded view of a robotic finger assembly in accordance with an embodiment of the invention such as may be used to implement the fingers of FIGS. 1-3.

At a second end of the link member 340, the finger assembly 300 includes another link member (link $l_3$) 350 that mimics the second digit of the human finger. The link member 350 is pivotally mounted to the link member 340 via pin or shaft 356 such that it may pivot about Axis 3. Hence, when actuated by cables or tension elements 321-324, the finger assembly 300 can produce independent movement of the digit/link member 350 relative to the digit/link member 340 about the shaft 356 (Axis 3) (e.g., like a human finger the second digit may move with the first digit held stationary or as this digit is also moving at the knuckle). One or more pulleys 354 may be provided on or as part of link member 350, with FIG. 4 showing a single pulley (i.e., $p_9$) formed as a part of the body of link member 350. The finger assembly 300 further includes another link member 370 that represents the third digit of a human finger and is pivotally mounted to the second digit or link member 350 via pin 364. The pivoting about Axis 4 or shaft 364 is tied to movement of link member 350 via link member 360 (link $l_5$), which is pivotally attached to both link members 340 and 370.

To better understand the design and operation of a finger assembly (such as assembled finger 300), it may be useful to show one useful arrangement for a finger for use with a robotic hand assembly in an exploded manner. FIG. 4 illustrates an exploded view of a single finger or finger assembly 400 as may be used in a hand assembly in accordance with the present invention (and used for finger 300 although other pulley arrangements, link member configuration, and design alterations may be used to provide the functionality of finger assembly 300). The base link (link member $l_0$) 410 of the finger 400 would be mounted to a palm plate (such as plate 124 of FIGS. 1 and 2) with mounting holes 418. The next link (link member $l_1$) 420 may take the form of a double clevis as shown. This allows it to be pivotally linked via holes 421 and Axis 1 shaft (shaft or pin $s_1$) 416 to the base link 410 at hole/passageway 417 while also being pivotally linked via holes 422 and Axis 2 shaft (shaft or pin $s_2$) 423 to link or first digit link (link member $l_2$) 430.

Link (link member $l_3$) 460 may be constructed as a unitary body or in two halves as shown, and link 460 represents a second digit of a human finger. Link 460 is pivotally mounted to the first digit link 430 via the Axis 3 shaft (shaft or pin $s_5$) 452 that extends through holes 450 and 462 in links 430, 460, respectively. The finger 400 further includes a link 480 (link member $l_4$) that provides a third digit of the finger 400 similar to a human finger. The link 480 is pivotally mounted to Axis 4 shaft (shaft or pin $s_6$) 474 that extends through hole 488 in third digit link 480 and hole 472 in the halves of second digit link 460. There is an additional link (link member $l_5$) 468 that is used to couple the motion of second digit link 460 and third digit link 480. The link 468 is pivotally mounted via shafts 458, 482 (shafts or pins $s_7$ and $s_8$) that extend into holes 454 and 484 in lines 430 and 480. The link 468 is also pivotally attached at its proximal end with pin or shaft 458 to the first digit link 430 via hole 454 (with its distal end attached to third digit link 480 via shaft 482). As a result of this mounting arrangement, movement of the third digit link 480 is coupled to movement or motion of the second digit link 460 (e.g., the link 480 curls inward with the link 460 and straightens with the link 460 but not independent of this second digit link).

As discussed above, the fingers formed in accordance with embodiments of the invention are actuated with a set of pulleys and tension elements arranged to achieve a form factor that allows the pulleys and tension elements to be housed or positioned within the human form factor of a finger. The finger 400, for example, typically would be actuated using tendons or cables that are tensioned and moved by a drive assembly (such as assembly 160 shown in FIG. 16). The cables are not shown in FIG. 4 but would extend through the holes 419 in base link or mounting block 410 and over the pulleys shown as part of finger 400 for termination or attachment on the links (as will be discussed for each of the four cables with reference to the following figures). In the embodiment, steel cables (e.g., SAVA Industries 2024 SN or the like) are used for tension elements. The steel cables operate over pulleys in the finger 400 and terminate in either first digit link 430 or second digit link 460.

With reference to FIG. 4, pulleys 411, 412, 413, and 414 (pulleys $p_1$ to $p_4$) are each single-groove idler pulleys that ride on Axis 1 shaft 416 (shaft or pin $s_1$), which extends through base link 410 via hole or passageway 417. Pulleys 436 and 434 (pulleys $p_5$ and $p_7$) are supported on and rotate about Axis 2 shaft 423 (shaft or pin $s_2$), which extends through a hole 432 in a first/proximal end of first digit link 430. Pulley 436 is a double-groove idler pulley while pulley 434 is a single-groove idler pulley. Pulley 438 (pulley $p_6$) is also a double-groove idler pulley, which is supported on and rotates about shaft 440 (shaft or pin $s_3$) that extends through hole 441 in first digit link 430 proximate to pulley 436. Pulley 442 (pulley $p_8$) is a double-groove idler pulley that is supported by and rotates about idler pulley shaft 448 (shaft or pin $s_4$) that extends through a hole 446 in a second/distal end of first digit link 430. In this design, pulley $p_9$ is machined into a half of the body of second digit link 460 (but it could also be designed as a separate idler pulley in which case it may be supported and rotate about Axis 3 shaft 452 (shaft $s_5$)). Retaining or guide plates 444 and 470 may be included to retain pulleys and/or cable on the first and second digit links 430, 460.

Figure 5:
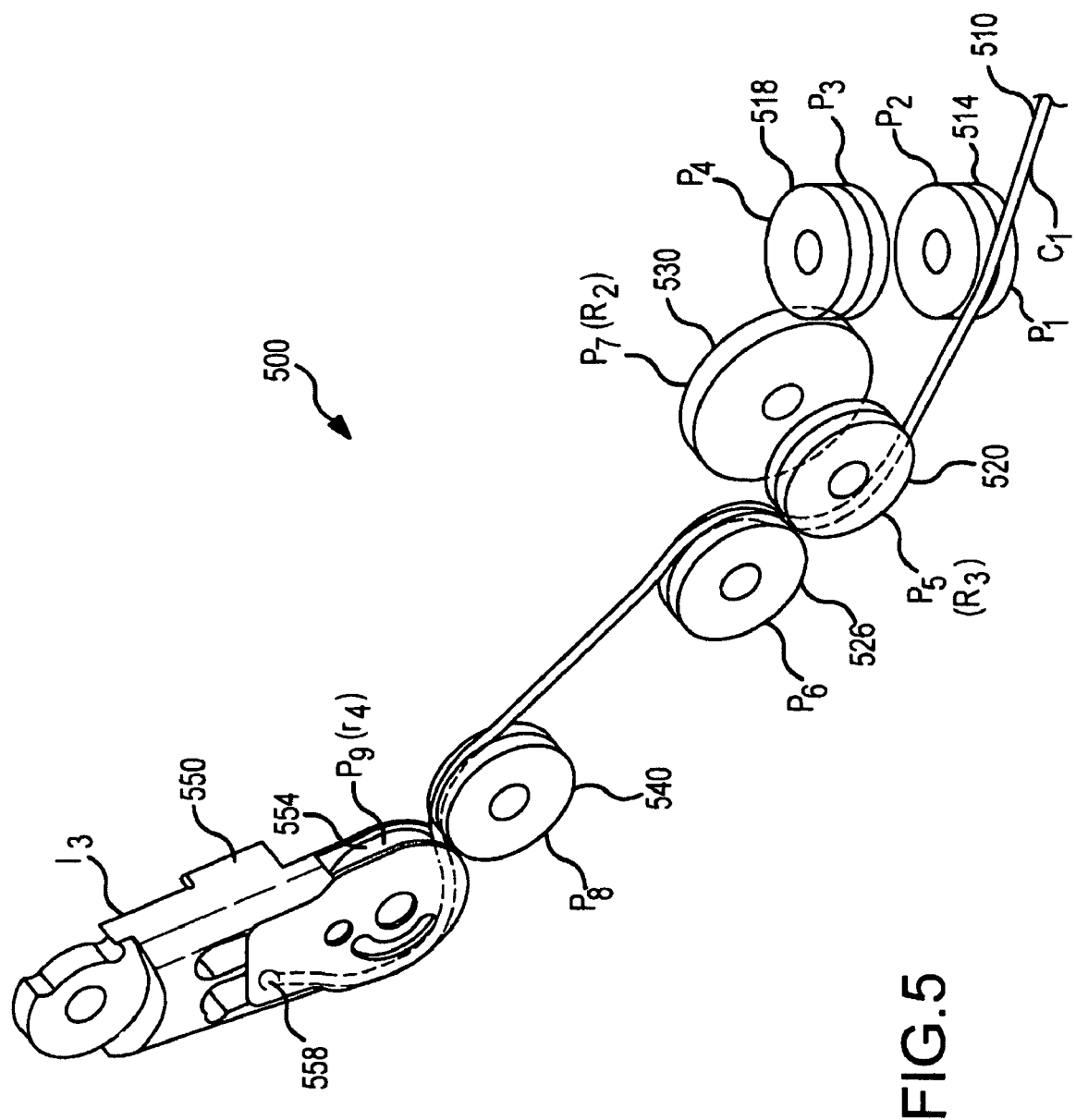
FIGS. 5-7 illustrate partial exploded views of a set of pulleys or a pulley assembly that may be included within a finger, such as the fingers of FIGS. 1-4, as they may be used to guide and/or support four tendons or cables used to drive or actuate the finger during operation of a finger assembly incorporating these pulley sets or assemblies.
Figure 6:
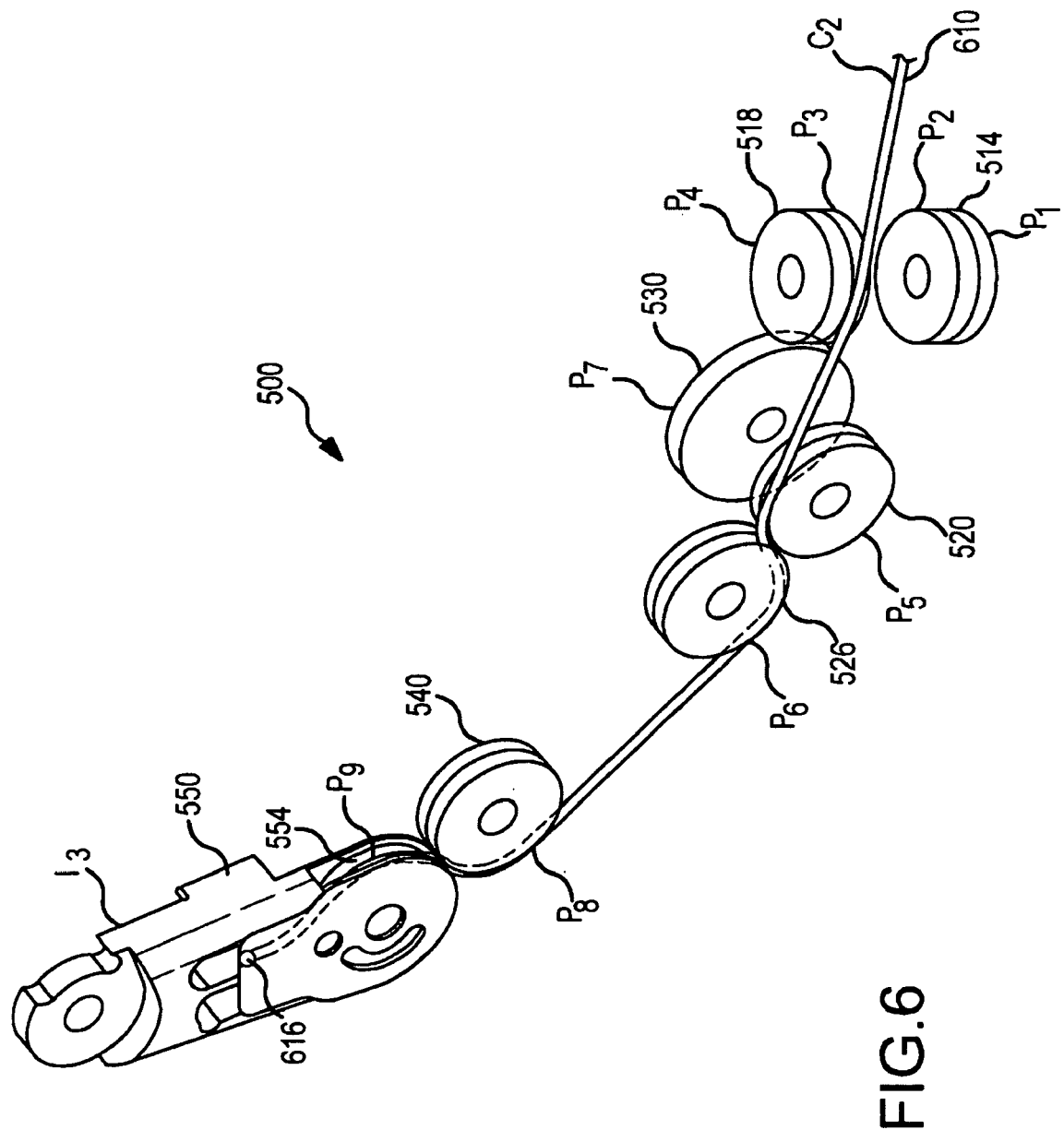
Figure 7:
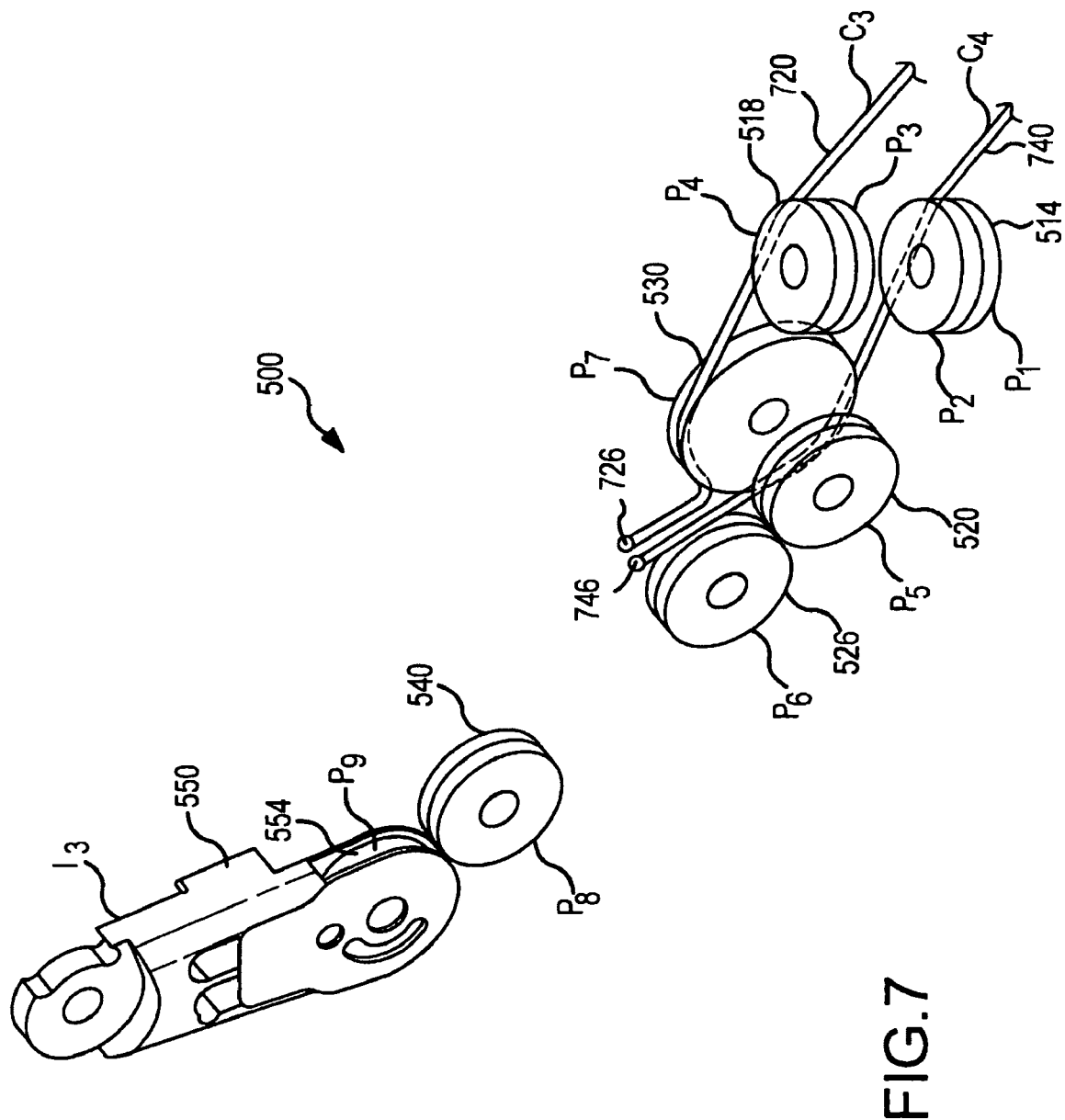

The robotic finger embodiments described herein are generally operated via four tendons or cables (e.g., tensioning elements that may take the form of steel cables or the like) in an "n+1" arrangement. That is, four tendons that remain in tension are used to actuate each finger's 3 degrees-of-freedom (DOF). FIGS. 5 to 7 present partial views of a robotic finger assembly 500 illustrating the pulley set and the second digit link to explain exemplary tendon or cable routing and/or termination or attachment within the robotic fingers of the invention. The four cables or tendons are labeled $c_1$ to $c_4$, and these may be the cables shown in FIG. 3 used to actuate the finger 300. As shown, the pulley set for the finger assembly 500 (which may be finger 300 or 400 for example) includes nine pulley elements 514, 518, 520, 526, 530, 540, 554 with some being single and some being double track pulleys to provide pulleys $p_1$ to $p_9$ as shown (e.g., pulley element or pulleys 514 represents two individual pulleys as does element 518 while elements 520, 526, and 540 are double-groove pulleys).

FIG. 5 shows the cable or tendon 510 (or cable $c_1$) and its routing in the pulley assembly of finger 500 as well as its termination point 558 on the body of second digit link 550 (link $l_3$). From the termination point 558 in link 550, the cable or tendon 510 passes around pulley 554 and makes an "S" shape to the opposite side of pulley 540 contacting one of the two tracks of this pulley 540. It continues to pulley 526 (again, contacting one of its tracks) and then wraps in another "S" shape around to the opposite side of pulley 520 against one of its two tracks. It continues to pulley p2 portion of pulley element 514 where it makes a slight bend towards the inside of the finger in order to maintain contact with pulley 514. Note, the cable 510 uses the inside groove or track of pulleys 520, 526, and 540. Also, significantly, the cable routing shown in FIG. 5 does not require or create any helixes (a full wrap around a pulley) but, instead, only calls for the cable 510 to wrap part way (such as less than 180 degrees of contact and, often, less than about 90 degrees of contact between the pulley and the tendon 510). This increases the number of pulleys required in the set of pulleys of finger 500, but it reduces the amount of friction while allowing the finger to conform to a human finger form factor (e.g., facilitates miniaturization).

FIG. 6 illustrates the finger assembly 500 with the tendon 610 (cable $c_2$) routed through the pulley set. The tendon 610 is shown to terminate in second digit link 550 at termination or mounting point 616 on the opposite side of pulley 554 as did the tendon 510 (cable $c_1$). It wraps partially around pulley 554 and makes an "S" shape to the opposite side of pulley 540. The tendon 610 continues on its routing to pulley 526 and makes another "S" shape onto pulley 520. It continues to pulleys 518 around which it makes a slight bend in order to maintain contact with pulley $p_3$. As shown, the tendon 610 uses the outside grooves of pulleys 520, 526, and 540, and the tendon 610 is not routed completely around any of the pulleys of finger assembly 500 (i.e., no helixes are formed) but only contacts a portion of each pulleys contact track or groove. Note, pulleys $p_1$, $p_2$, $p_3$, and $p_4$ are individual pulleys that can rotate independently (and not four different grooves in two pulleys).

FIG. 7 illustrates the finger assembly 500 with tendons 720 and 740 (cables $c_3$ and $c_4$) routed through the pulley set. Tendon 720 terminates at 726 in the first digit link $l_2$ (not shown in FIG. 7 for ease of illustrating cable routing but it may be link 430 of finger assembly 400 or link 340 of assembly 300). The tendon 720 extends from link $l_2$ over a portion of pulley 530. It continues onto pulley $p_4$ portion of pulley element 518, where it makes a slight wrap towards the inside of the finger 500 in order to maintain contact with pulley element 518. Tendon 740 (cable $c_4$) also terminates on first digit link $l_2$ at 746, but it continues onto the opposite side of pulley 530 as tendon 720. Tendon 740 then is routed to pulley $p_1$, where it makes a slight wrap or bend towards the inside of the finger 500 to maintain contact with pulley $p_1$. Again, the cables are not wrapped in a helix shape about any of the pulleys of finger 500, and none of the cables rub against themselves or each other, which limits friction and increases longevity of the finger 500.

Figure 8:
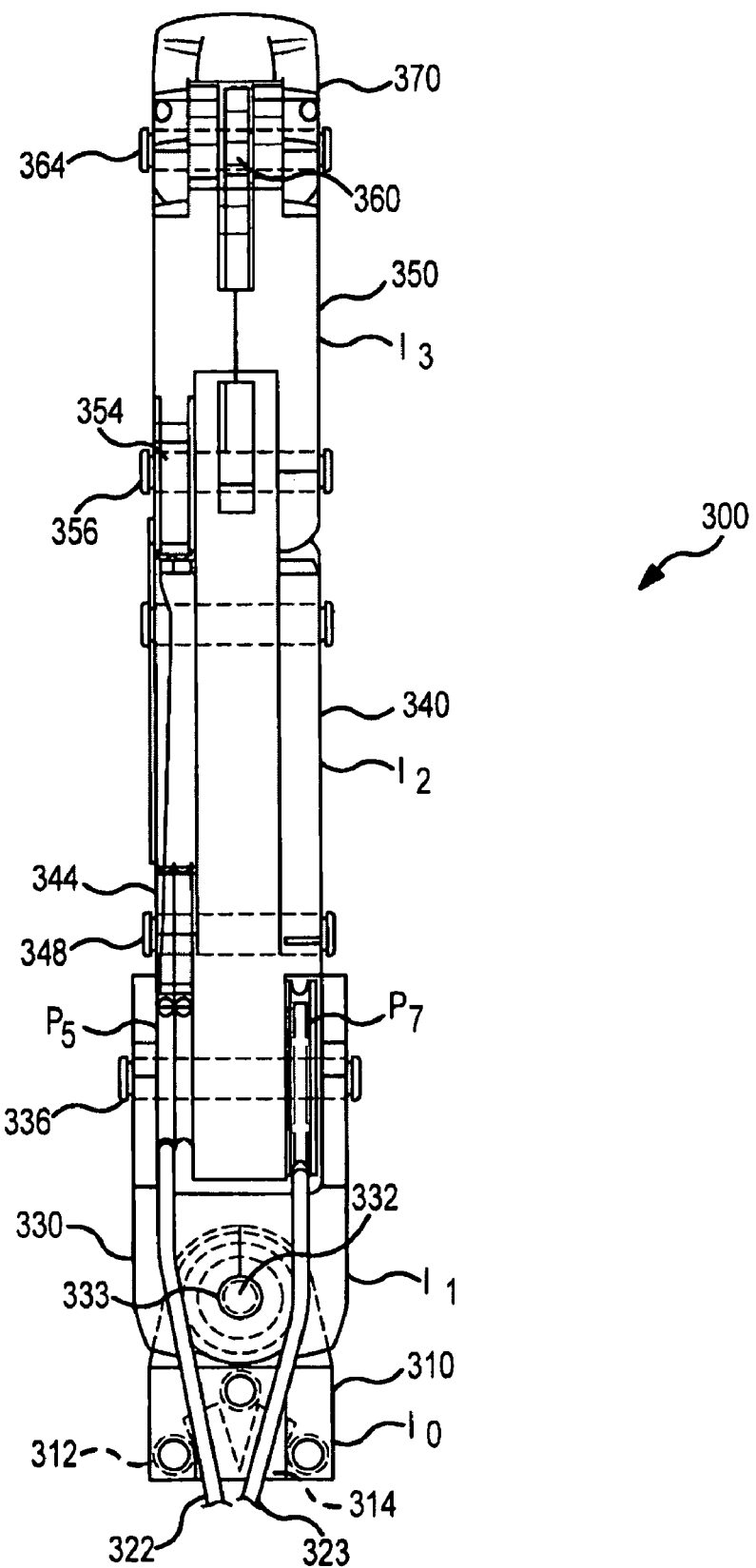
FIG. 8 illustrates side view of the robotic finger assembly of FIG. 3 illustrating a arrangement of the base or attachment link ($l_0$) that feeds the tendons or drive cables into the finger at angles (e.g., a tendon input angle or the like)

FIG. 8 illustrates an orthogonal view of the finger assembly 300 of FIG. 3 (which may be designed with the arrangement of pulleys and the cable routing shown in FIGS. 3 and 4, respectively). The assembly 300 is shown to include the cables 322, 323 extending into holes or passageways 314 in base link member 310 to contact pulleys in link member 330 (link $l_1$) and then pulleys in first digit link 340 (i.e., pulleys $p_5$ and $p_7$ supported on link $l_2$). As can be seen, the cable guide holes or passageways 314 in block or base link 310 are angled outward from the face or side of the link body 310 where the cables 322, 323 are received so as to accommodate the slight wrap about pulleys $p_1$, $p_2$, $p_3$, and $p_4$ made by tendons $c_1$ to $c_4$ (with only cables 322, 323 being visible in FIG. 8). The angling assists in maintaining the desired contact between a portion of each of the pulleys $p_1$ to $p_4$ and cables $c_1$ to $c_4$.

Figure 9:
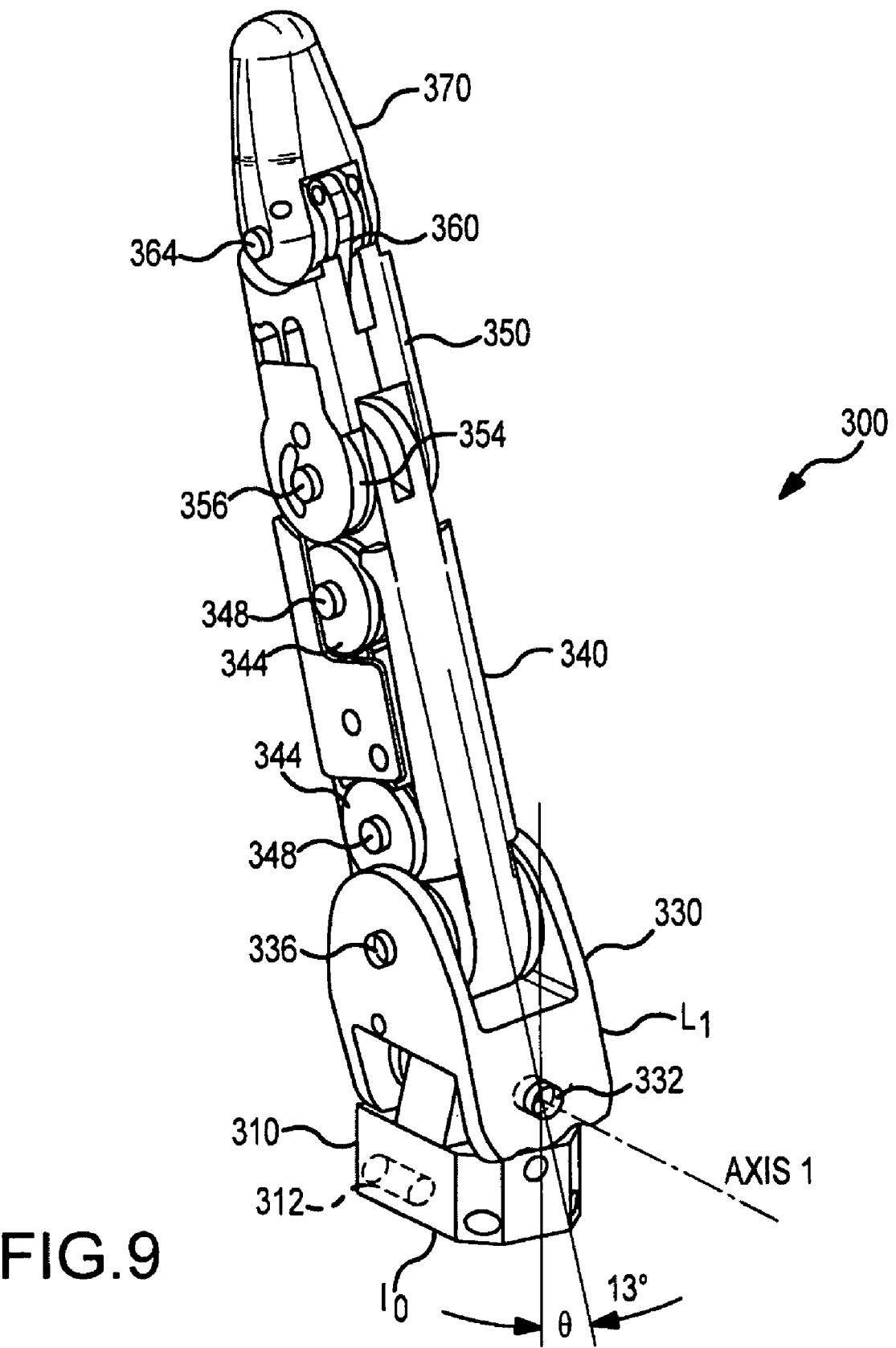
FIGS. 9-14 illustrate the finger assembly of FIG. 3 in a number of positions or operating modes showing the range of motion of the finger and its digits and independent movement of such digits to actuate the finger in a more human-like manner.
Figure 10:
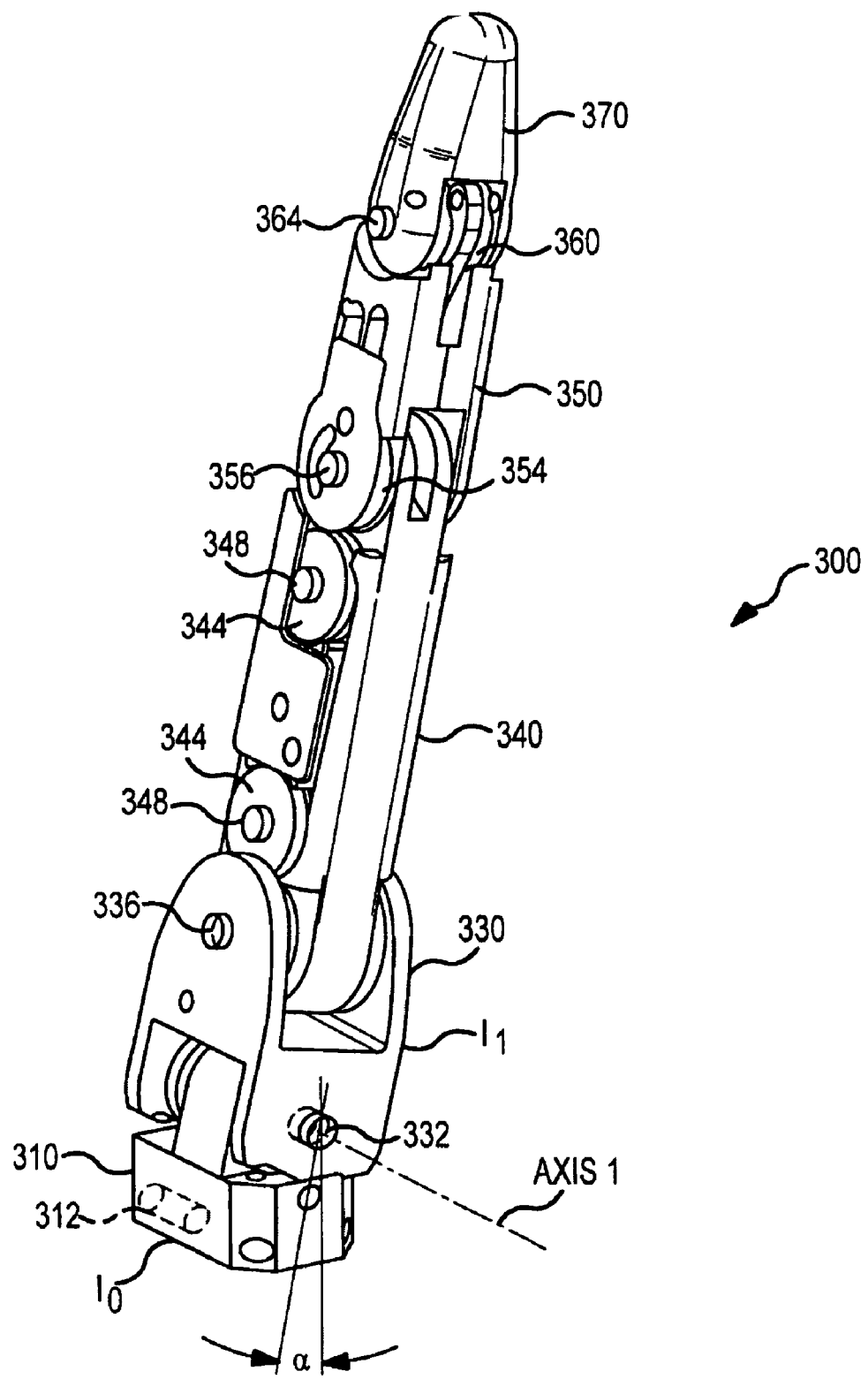

The fingers of embodiments in accordance with the invention, such as those adapted as shown with finger assembly 300, may be designed to provide a range of motion of each of the finger digits/segments that is similar to that found or obtained with a human finger. FIGS. 9-14 show the finger assembly 300 in a variety of positions or modes of operation that are achievable due to the arrangement of the joints and by actuation through movement by the drive assemblies of tension elements or cables over the included pulleys. Specifically, FIGS. 9 and 10 illustrate the side-to-side range of motion provided for the finger assembly 300 as is found in the human finger at the knuckle. For example, FIG. 9 shows the finger 300 in a first side position (left-most position) while FIG. 10 shows the finger 300 in a second side position (right-most position). These figures show the link 330 (link $l_1$) as it fully pivots side-to-side on pin or shaft 332 or rotating about Axis 1 of the finger 300.

FIG. 9 shows the rotation to be at a maximum angle, θ, which may be less than about 20 degrees such as about 13 degrees as shown (negative or positive rotation depending on the orientation with the rotation appearing negative or counterclockwise in FIG. 9). FIG. 10 shows the rotation to be at a maximum angle, α, in the other or opposite direction (e.g., clockwise or a positive angle of rotation relative to an orthogonal plane extending upward through Axis 1). This may be about the same magnitude as the rotation in the other direction for symmetric side-to-side movement or it may differ some amount. In one example, the rotation angle, α, is also less than about 20 degrees or about 13 degrees as shown. FIGS. 9 and 10 show the range of motion of link $l_1$ relative to link $l_0$ about Axis 1 to be about plus or minus 13 degrees. At the extremes of motion, contact may be made between the flats on link $l_1$ and link $l_0$ (e.g., a portion of the body of link 330 may abut or contact a proximate surface of block or base link 310 to act as a limit or stop to rotation of the link 330 about pin or shaft 332).

Figure 11:
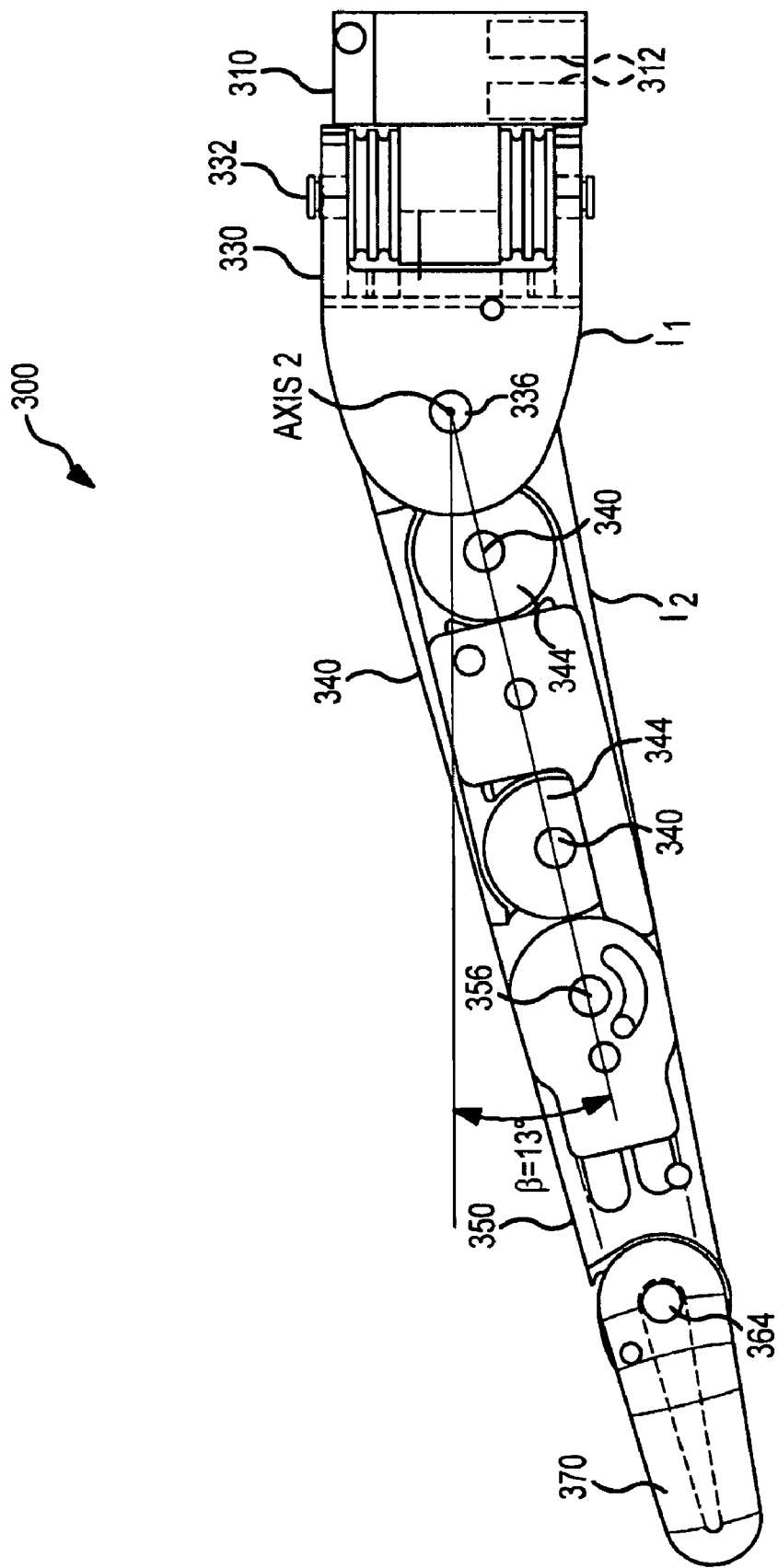
Figure 12:
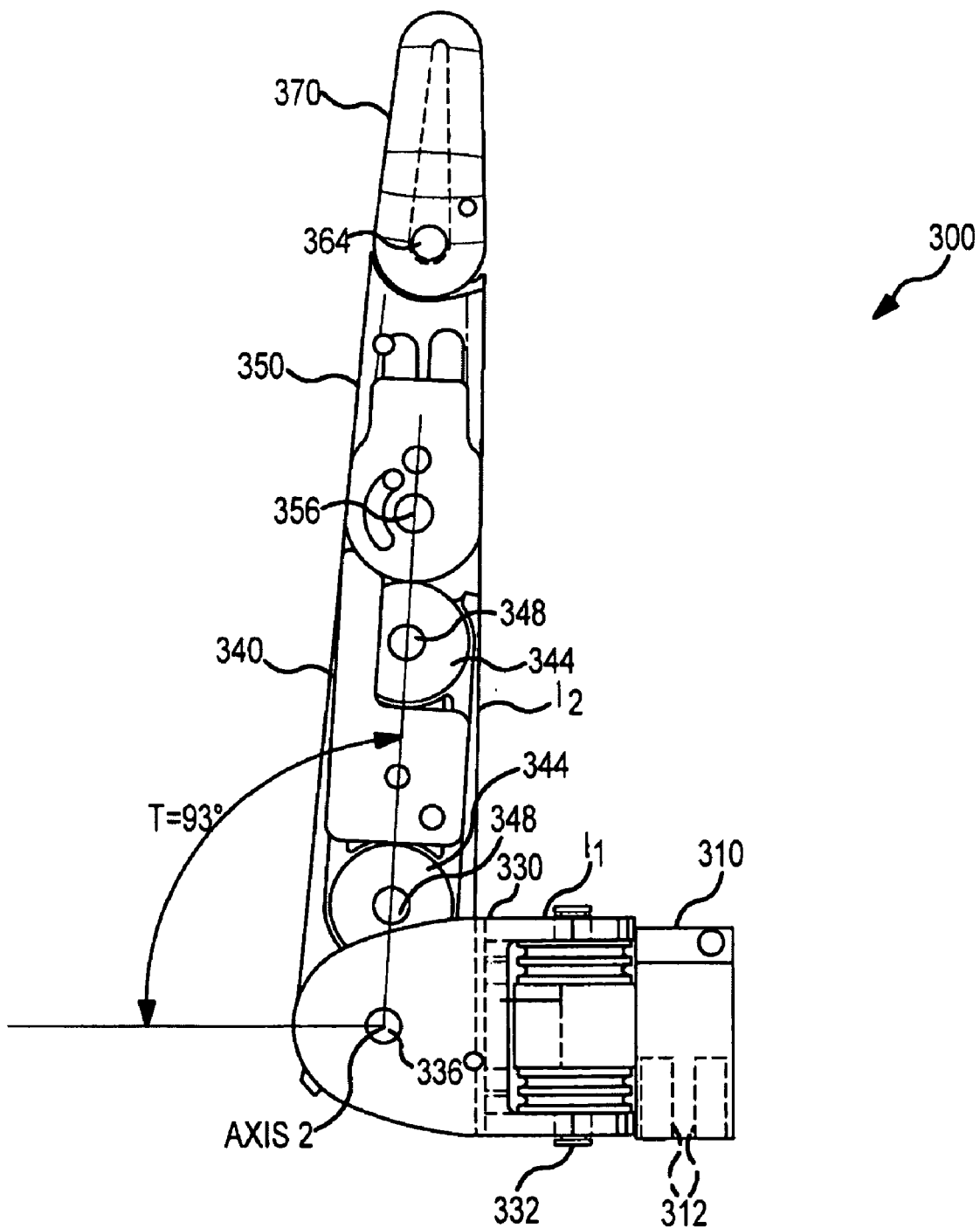

FIGS. 11 and 12 illustrate the finger assembly 300 in first and second vertical positions (e.g., positions relative to a horizontal plane passing through pin 336 in link 330), with FIG. 11 showing the finger 300 in bent back position (the first digit link 340 bent away from the palm plate) and FIG. 12 showing the finger in a fully bent forward position (the first digit link 340 bent inward toward the palm plate). The fingers of the human hand do not extend very far backward or away from the palm, and, hence, the finger 300 is shown in FIG. 11 to have a first vertical position associated with maximum backward bending with a relatively small angle of rotation, β, such as less than about 20 degrees (counterclockwise or negative rotation relative to pin 336) and, in one example, about 13 degrees. Also, in this position, the digits of the finger 300 are generally straight or in a line with links 340, 350, and 370 generally aligned or with their longitudinal axes being planar but in some cases, second digit link 350 and third digit link 370 may arch backward further than first digit link 340 similar to the human finger. Travel to this vertical position may be limited with a stop on link 330 or link 340 or, in some cases, travel in this direction is limited by operation of the tension elements or cables (or by operation of drive motors).

In contrast, the human fingers can be curled inward toward the palm to form a fist or to grasp objects. With this in mind and as shown in FIG. 12, the finger assembly 300 is designed to allow the first digit link 340 (or link $l_2$) to rotate through a relatively large angle of rotation, τ, about pin or shaft 336 (Axis 2) such as a clockwise rotation to the second vertical position shown of at least about 75 degrees and more typically to at least about 90 degrees (with 93 degrees shown). When considered together, FIGS. 11 and 12 show the range of motion of link $l_2$ relative to link $l_1$ about Axis 2, and this range may be about negative 13 degrees (counterclockwise rotation) to about positive 93 degrees (clockwise rotation) or more.

Figure 13:
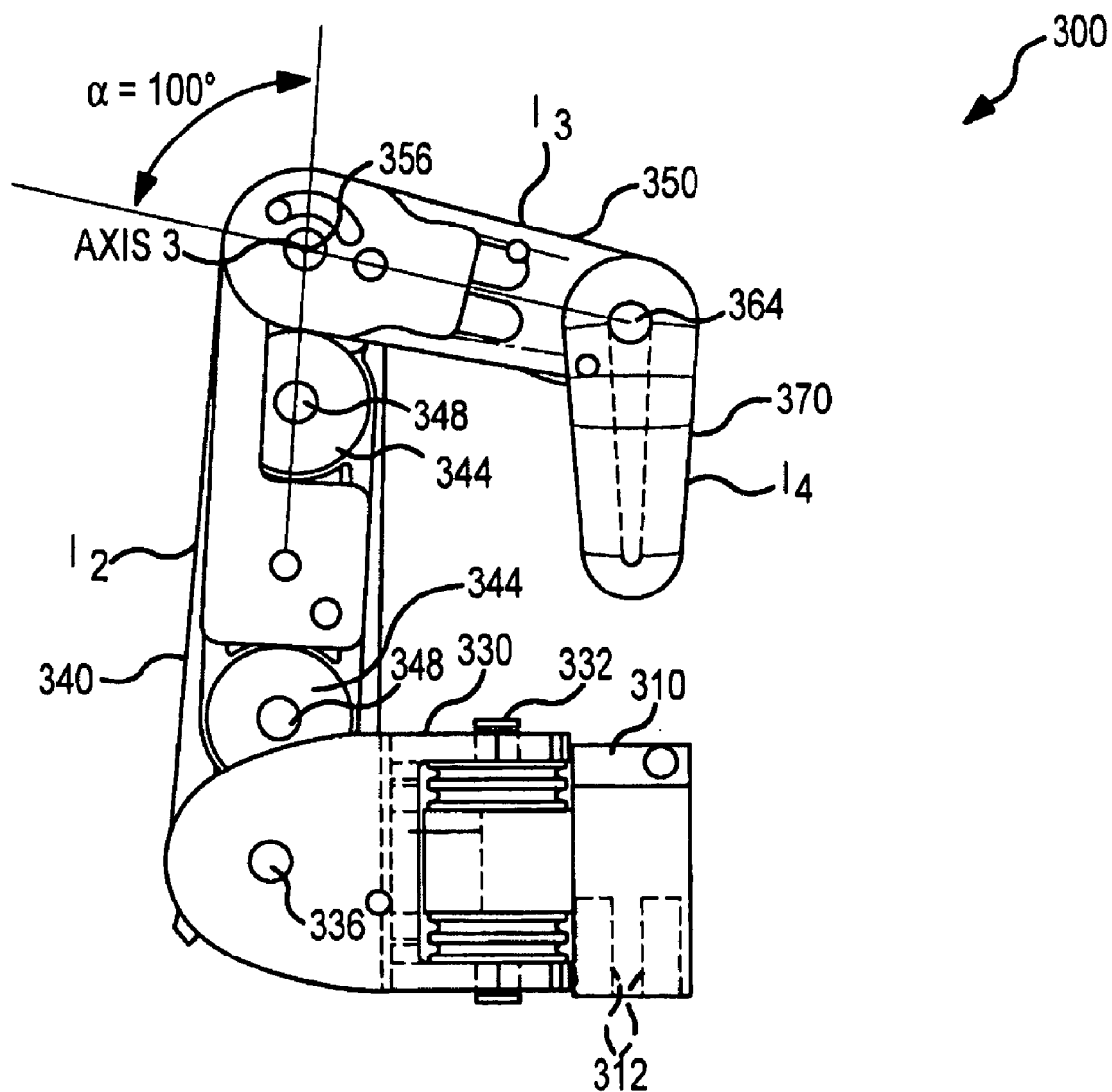

As discussed above, the second digit link 350 (link $l_3$) may be independently actuated relative to the first digit link 340 (link $l_2$). FIG. 13 shows the finger assembly 300 in a closed or fully curled inward position with the second digit link 350 rotated about pin 356 or Axis 3 to a positive rotation (clockwise) angle, α, of at least about 90 degrees and more typically at least about 100 degrees. In other words, the second digit link 350 has a range of motion about Axis 3 or shaft 356 of about 0 to 100 degrees.

Figure 14:
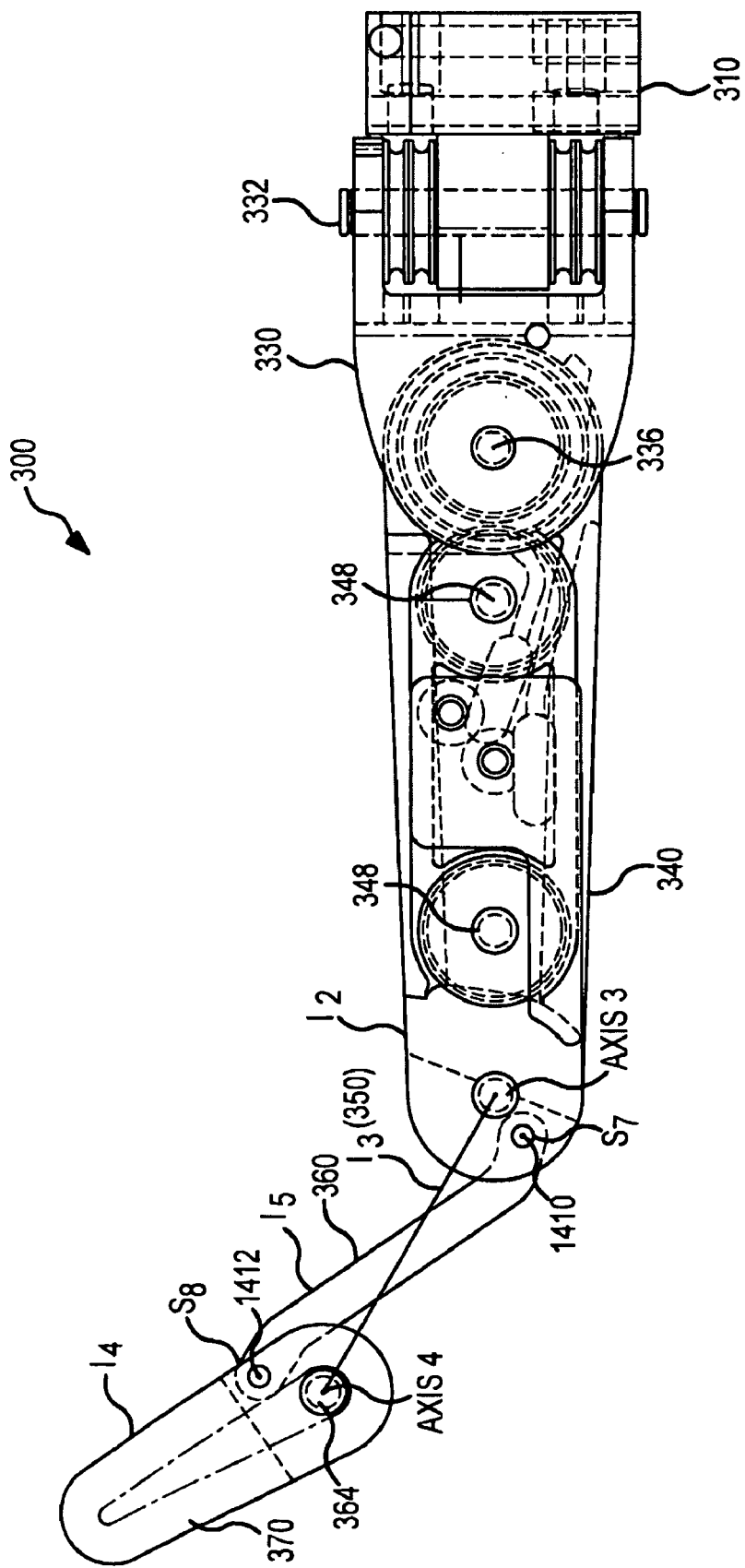

In some embodiments, the third digit link 370 (link $l_4$) is coupled to the second digit link 340 (link $l_3$) as a slave linkage. It will be seen in FIG. 13 that the third digit link 370 (link $l_4$) is rotated relative to or with link 340 (link $l_3$). FIG. 14 illustrates the finger assembly 300 with the second digit link 350 or $l_3$ as a line to better show link 360 (link $l_5$). This rotation is a passively coupled rotation and is a function of the rotation of the second digit link 350 (link $l_3$) to the first digit link 340 (link $l_2$). As will be understood from FIG. 14, link 360 (link $l_5$) pivots about third digit link 370 (link $l_4$) at shaft or pin 1412 (shaft $s_8$) and about first digit link 340 (link $l_2$) at shaft 1410 (shaft $s_7$). The distances between shaft 1410 (shaft $s_7$) and Axis 3 on link 340 may be set to be about approximately 1.3 times less than the distance between shaft 1412 (shaft $s_8$) and Axis 4 on link 370. Note, this type of coupling may also be achieved using pulleys and cables.

The motion of each of the finger joints is related to the motion of each tendon. If each joint position is labeled q1, q2, q3 corresponding to relative link motions about Axes 1, 2, and 3, respectively. The velocities of each joint are given by qi, where the units would be radians/second. The velocities of each cable are given by ci, where the units would be meters/second. If the radius of each pulley is given in meters, then we have the following relationship:

$$\begin{pmatrix} \dot{c}1 \\ \dot{c}2 \\ \dot{c}3 \\ \dot{c}4 \end{pmatrix} = \begin{bmatrix} r1 & -r3 & -r4 \\ r1 & r3 & r4 \\ -r1 & r2 & 0 \\ -r1 & -r2 & 0 \end{bmatrix} \begin{pmatrix} \dot{q}1 \\ \dot{q}2 \\ \dot{q}3 \end{pmatrix}$$

Note, that the motions of the tendons are not independent. That is, the three joint velocities define the velocities of all four tendons if they are to remain in tension. Stated otherwise, if any three of the four tendon velocities is commanded, the fourth tendon velocity is defined by the above equation. If velocities were to excessively vary from the relationships defined by the equation, the tendon would either stretch or lose tension.

Figure 15:
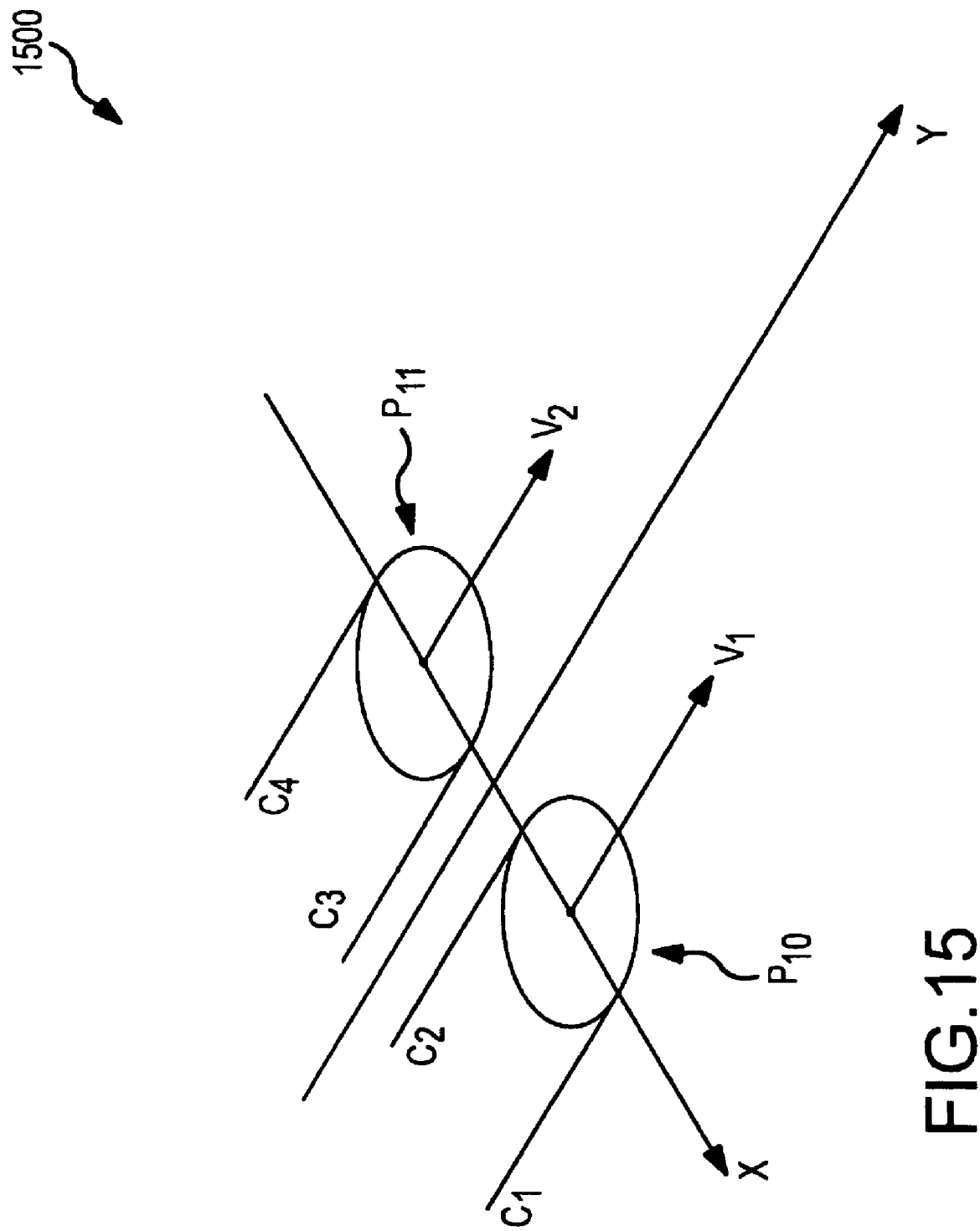

As noted above, the motion of the tendons or cables is not independent. One way to operate the finger tendons would be to connect each tendon to an independent linear actuator. In this case, the motion of the four actuators would need to be coordinated to maintain the relation in the above equation and simultaneously maintain cable tension. Another approach is to use a mechanism to enforce this relation so that only three actuators or motors are required to drive each finger of the robotic hands described herein. Such a mechanism 1500, which may be thought of as a passive tension maintenance mechanism, is shown schematically in FIG. 15. Here, tendons $c_1$ and $c_2$ form a loop that is supported by pulley $p_{10}$. Tendons $c_3$ and $c_4$ are made to form a loop supported by pulley $p_{11}$. The desired relationship is then enforced via a mechanism (not shown) that forces the axis of the pulleys $p_{10}$ and $p_{11}$ to travel parallel to the y-axis in FIG. 15. The velocities of each pulley along this axis, $v_1$ and $v_2$, are equal and opposite (e.g., $v_1 = -v_2$).

In this case, the kinematic relationship of the previous joint to tendon mapping equation will be satisfied, and only three of the four tendons need to be actuated via controlled actuators or drive motors in order to drive the finger. In the initial positions of pulleys $p_{10}$ and $p_{11}$ are set such that there is an initial tension in the cable, then that tension can be maintained passively. If the tendons $c_1$, $c_3$, and $c_4$ are driven using actuators $m_1$, $m_2$, and $m_3$, where the direction of positive motion is the same, then the following relationship exists (with positions having units of meters and indicated without dots over the letters/symbols and velocities ($\dot{m}$ i and $\dot{q}$, i) having units of meters/second with dots shown over the letters/symbols):

$$\begin{pmatrix} \dot{m}1 \\ \dot{m}2 \\ \dot{m}3 \end{pmatrix} = \begin{bmatrix} r1 & -r3 & -r4 \\ -r1 & r2 & 0 \\ -r1 & -r2 & 0 \end{bmatrix} \begin{pmatrix} \dot{q}1 \\ \dot{q}2 \\ \dot{q}3 \end{pmatrix}$$

Figure 16:
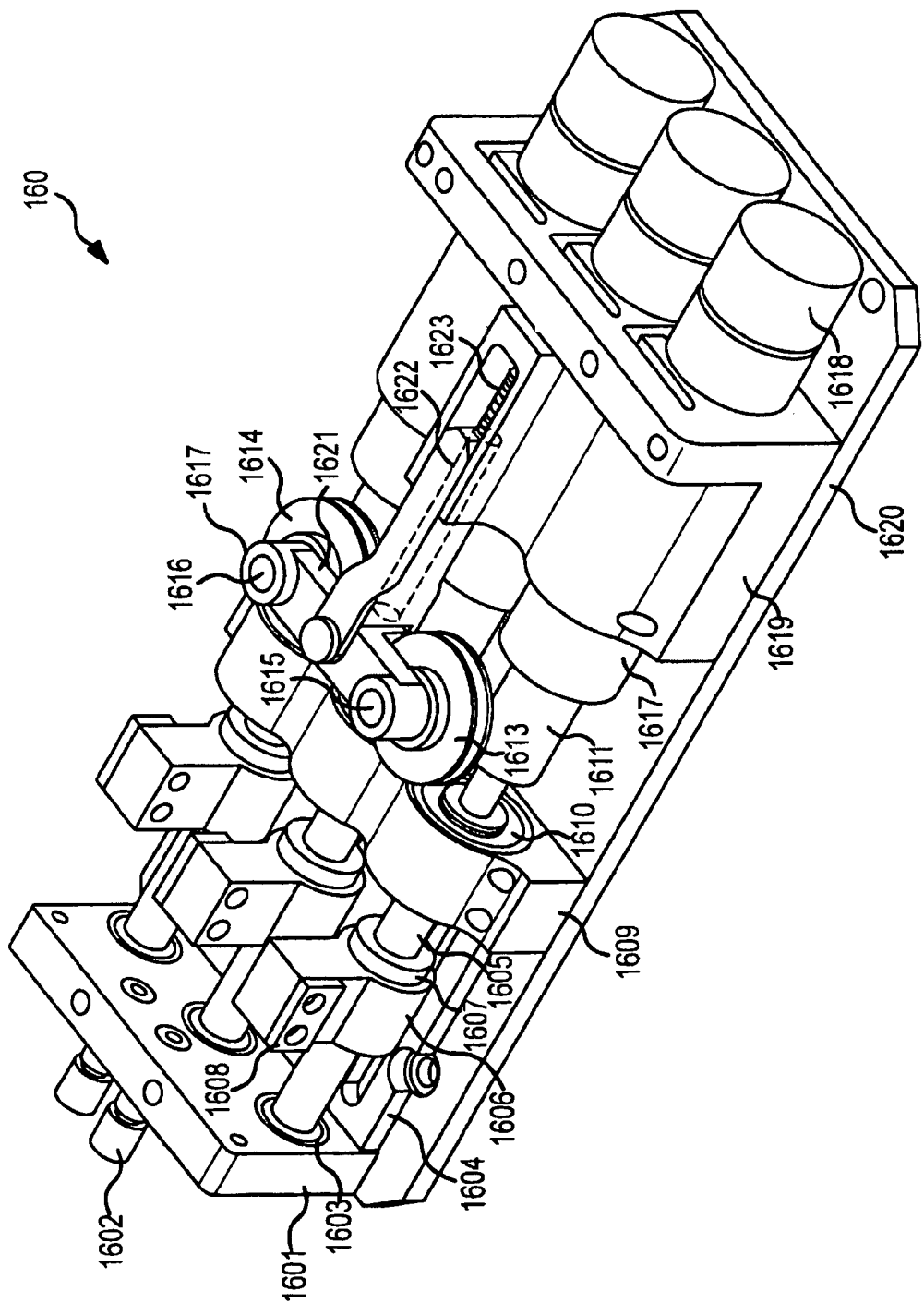
FIG. 16 is a perspective view of one of the finger drive assemblies or mechanisms of the system of FIG. 1 that may be used to independently actuate a finger assembly connected with a set of tendons or drive cables.

FIG. 16 illustrates the finger drive assembly or mechanism 160, and this mechanism 160 is adapted to implement the passive tension maintenance mechanism described above that allows three actuators (or drive motors in this example) to be used to operate or drive four tension elements or tendons/cables. The system or assembly 160 includes three actuators 1617 that may be provided with brushless DC motors or the like that are held in motor housing 1619, which in turn may be affixed to a base plate 1620. Each motor 1617 in some applications may have an encoder 1618 to record or determine rotary position for accurate control of a linked finger assembly. The output shaft of each motor 1617 is coupled to a lead screw 1605 via a flexible coupling 1611, which may be adapted to accommodate misalignment between the drive shaft and the lead screw 1605. The lead screw 1605 is supported by a front bearing 1603 and a rear bearing 1610, which supports thrust loads on the lead screw 1605.

The lead screw 1605, which is supported or retained by collar 1609, drives a nut 1607, which is mounted in a block 1606. This block 1606 is prevented from rotation by way of a "tongue" that rides in a grooved plate 1604. In one embodiment, the grooved plate 1604 is made from acetal, which provides a low-friction sliding surface. Each block 1606 is mounted with a clamp plate 1608 that is used to secure a cable tendon through which linear motion is transmitted. The passive tension maintenance mechanism is provided with two pulleys 1613 and 1614 that are mounted to a pivoting arm 1621 via shafts 1615 and 1616. The pivoting arm 1621 pivots on a link 1622, which is constrained to slide in a slot in motor mount 1619. The motion of link 1622 is constrained by a tensioning screw 1623 that is captured in a hole in motor mounting block 1619. The pivoting action of arm 1621 very closely approximates the constraint in the equation $v_1=-v_2$ over the range of motion of the finger.

Figure 17:
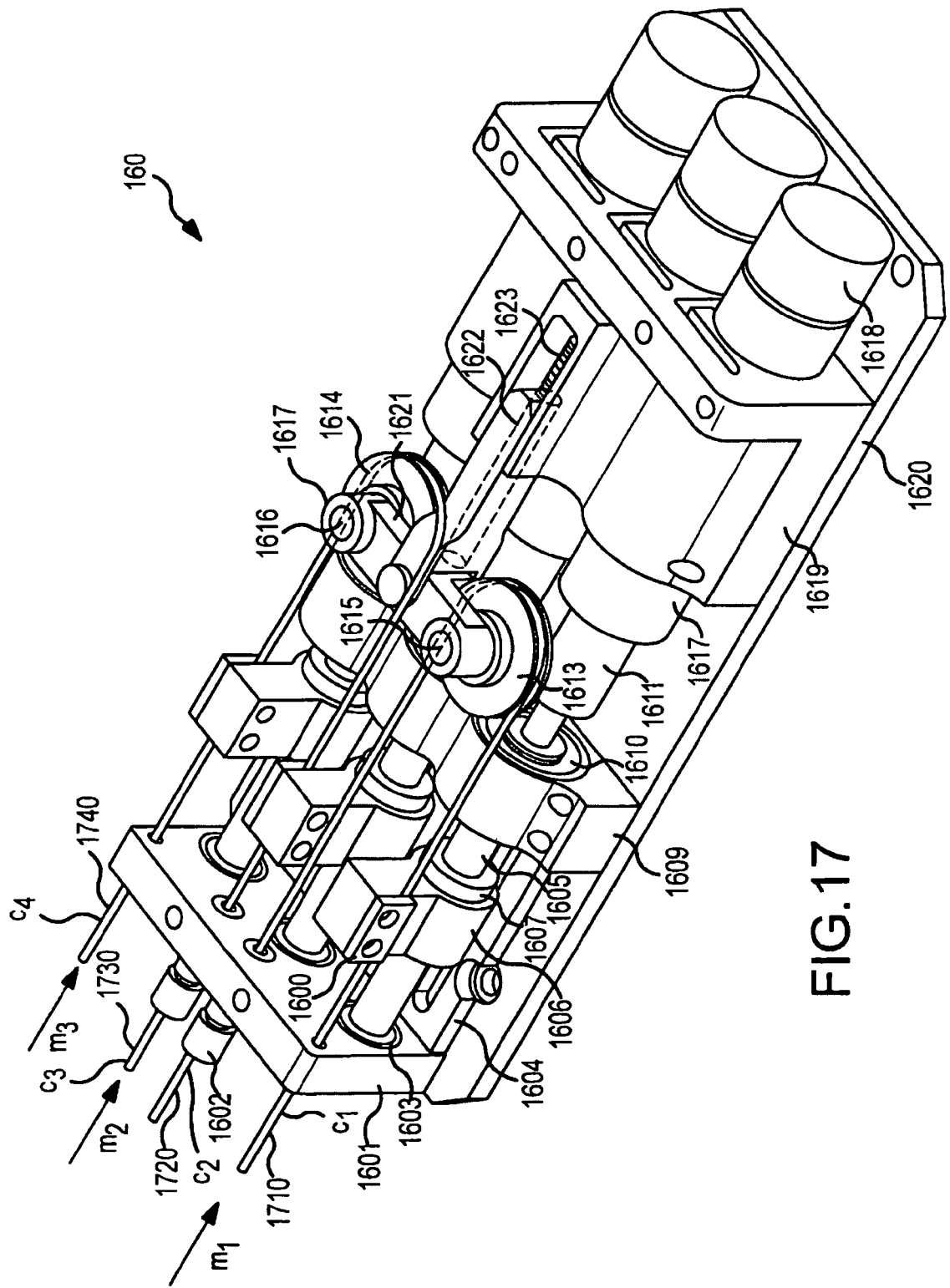
FIG. 17 shows the finger drive assembly of FIG. 16 including wire or cable that may be driven by a motor set to provide a set of four tendons or drive cables for a finger assembly of a robotic hand in accordance with an embodiment of the invention.

FIG. 17 shows the finger driving mechanism 160 with the tendons or cables 1710, 1720, 1730, 1740 (or cables $c_1$ to $c_4$) routed through the passive tension maintenance mechanism. The cables 1710, 1720, 1730, 1740 are passed through holes in the bearing support block 1601 to pulleys 1613 and 1614. By tightening the tensioning screw 1623, the finger tendons 1710, 1720, 1730, 1740 may be tensioned. Additional adjustments 1602 on bearing support block 1601 may be used to fine tune the position of the finger joints relative to the lead screw nuts 1607.

Figure 18:
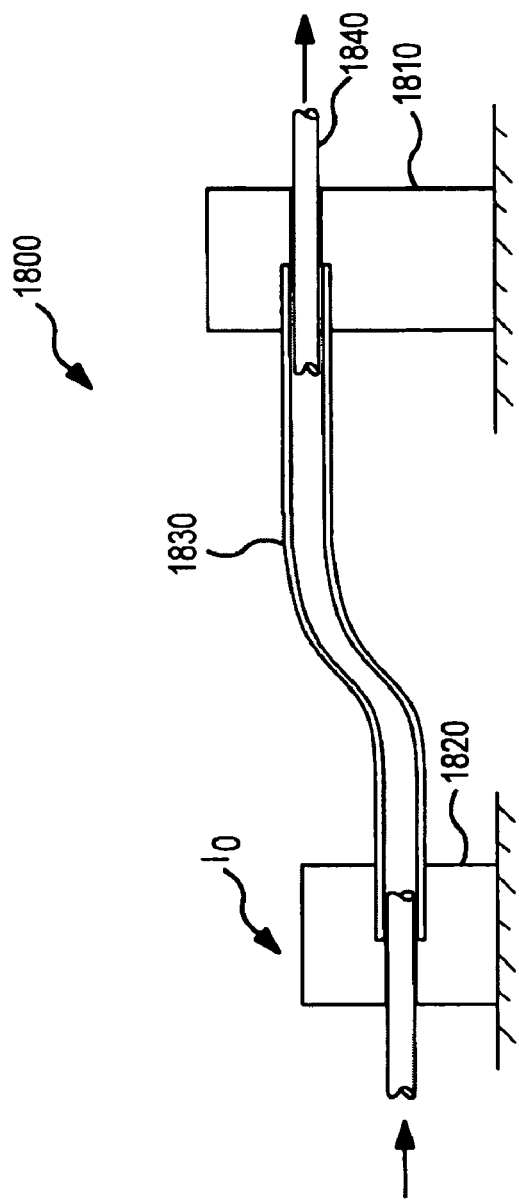
FIG. 18 illustrates schematically a partial view of a tendon mounting assembly used in robotic hands in accordance with embodiments of the invention, such as in the hand shown in FIGS. 1 and 2.
Figure 19:
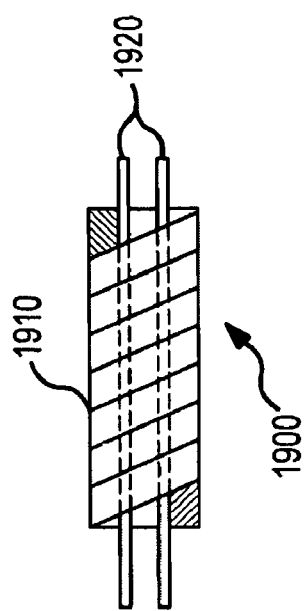
FIG. 19 illustrates one embodiment of a flexible conduit that may be used to guide/support the tendons or drive cables of a robotic hand system.

In the prior description, it was generally assumed that the length of the tendons or cables between the finger assembly and the finger drive assembly remains constant. However, it is expected that the drive assembly and the finger assemblies may be mounted on opposite sides of a wrist joint and the length of the cables may not be constant. To support such an implementation, flexible tendon conduits may be used to maintain the constant length constraint. For example, FIG. 18 shows a cable or tendon connection assembly 1800 with a flexible conduit 1830 mounted at one end to a bearing support block 1810 at the drive assembly and at another end to a base link 1820 (link $l_0$ of a finger assembly). The cable tendon 1840 then extends through this conduit 1830. The conduit 1830 supports a compression load that is equal in magnitude to the tension in the tendon 1840. FIG. 19 illustrates one implementation of a flexible conduit 1900, and, as shown, this embodiment utilizes a conduit 1900 that is formed from a square stainless steel wire or coil 1910 that provides the advantage of having smooth internal and external surfaces. The conduits 1910 are lined with a fiberglass fiber impregnated Teflon-liner tube or the like 1920, which reduces friction between the steel tendons (such as tendon 1840) and the conduit 1910 (or conduit 1830). Further, the interface between these components may be lubricated using a Teflon or other lubricant.

Although the invention has been described and illustrated with a certain degree of particularity, it is understood that the present disclosure has been made only by way of example, and that numerous changes in the combination and arrangement of parts can be resorted to by those skilled in the art without departing from the spirit and scope of the invention, as hereinafter claimed.

I claim:

1. A robotic hand, comprising:
   at least one finger assembly; and
   for each of the finger assemblies included in the robotic hand, a drive assembly selectively applying tension to four elongated and flexible tension elements;
   wherein each of the finger assemblies comprises a set of links actuated by the tension elements;
   wherein the links are interconnected with pivotal joints to have motion with three degrees-of-freedom;
   wherein the finger assembly further comprises a set of pulleys supported on the links to support and guide the tension elements in the finger assembly, the tension elements extending only partially about any one of the pulleys, whereby the finger assembly provides n+1 actuation with non-helical wrapping of the tension elements; and
   wherein the drive assembly consists of three actuators driving the four tension elements.

2. The robotic hand of claim 1, wherein at least a portion of the pulleys are single groove pulleys without helical wrappings and wherein the tension elements each comprise a cable.

3. The robotic hand of claim 2, wherein each of the cables wraps around less than half of the circumference of any of the pulleys.

4. The robotic hand of claim 1, wherein the set of links comprises a first digit link, a second digit link, and a third digit link, the third digit link being pivotally mounted to the second digit link and the second digit link being pivotally mounted to the first digit link, and wherein the first and second digit links are independently operable by the drive assembly applying tension to the tension elements.

5. The robotic hand of claim 4, the finger assembly further comprising a palm plate, a base link member, and a first digit mounting link member, wherein the base link member is rigidly attached to the palm plate to support the finger assembly, wherein the first digit mounting link member is pivotally mounted to the base link member for pivoting about a first axis, and wherein the first digit link is pivotally coupled to the first digit mounting link member for pivoting about a second axis transverse to the first axis.

6. The robotic hand of claim 5, wherein a range of motion for the first digit mounting link member relative to the base link member is less than about 40 degrees to define a side-to-side movement of the first digit link and wherein a range of motion of the first digit link relative to the first digit mounting link member is less than about 15 degrees rotation about the second axis in a counterclockwise direction relative to a plane extending through the second axis and in a clockwise direction relative to the plane extending through the second axis is in the range of about 75 to 100 degrees.

7. The robotic hand of claim 4, wherein first and second ones of the tension elements terminate on the second digit link and wherein third and fourth ones of the tension elements terminate on the first digit link.

8. The robotic hand of claim 4, wherein the finger assembly further comprises an additional link coupling the third digit link to the second digit link such that the third digit link is actuated by movement of the second digit link as a passive follower link.

9. The robotic hand of claim 1, further comprising an articulated wrist positioned between the finger assemblies and the drive assembly of each of the finger assemblies.

10. The robotic hand of claim 9, further comprising cable conduits extending through the articulated wrist and wherein each of the tension elements extends through one of the cable conduits.

11. A finger assembly for a robotic hand adapted to be driven by four drive cables, comprising
    a base link for receiving the drive cables and mounting to a base of the robotic hand;
    a mounting link pivotally mounted to the base link for rotation about a first axis;
    an elongated first digit link pivotally mounted at a first end to the mounting link for rotation about a second axis that is transverse to the first axis;

a second digit link pivotally mounted at a first end to a second end of the first digit link for rotation about a third axis; and a third digit link pivotally mounted to a second end of the second digit link for rotation about a fourth axis, wherein the first axis is substantially orthogonal to the second axis and the second, third, and fourth axes are substantial parallel.

12. The assembly of claim 11, wherein a pair of the drive cables are attached to the second digit link and a pair of the drive cables are attached to the first digit link and wherein the third digit link is coupled to the second digit link to be actuated to rotate about the fourth axis by movement of the second digit link about the third axis.

13. The assembly of claim 11, wherein the mounting link has a range of motion about the first axis of less than about 40 degrees.

14. The assembly of claim 13, wherein the first digit link has a range of motion in a first direction about the second axis of less than about 20 degrees and in a second direction of more than about 75 degrees and wherein the second digit link has a range of motion in the second direction of more than 90 degrees.

15. The assembly of claim 11, further comprising a plurality of pulleys on the one or more of the links, wherein each of the drive cables is routed through the finger assembly to contact one or more of the pulleys within a groove over less than one half of the pulley circumference and wherein at least one of the pulleys is a single groove pulley.

16. A robotic hand system, comprising:
a robotic hand assembly comprising a palm element and a plurality of fingers affixed to the palm element, wherein the fingers comprise a set of links and joints adapted to provide the finger with three degrees-of-freedom (DOF) movement;
a set of four drive cables for actuating each of the fingers to perform the three DOF movement; and
a finger drive mechanism for each of the fingers comprising a passive tension maintenance system maintaining each of the drive cables under tension and comprising three actuators selectively applying additional tensile forces on the drive cables to actuate the finger.

17. The system of claim 16, wherein the passive tension maintenance system comprises a first and second pulley, a first pair of the drive cables are connected together and looped over the first pulley, a second pair of the drive cables are connected together and looped over the second pulley, and the first and second pulley are positioned within the finger drive mechanism to place each of the cables under tension.

18. The system of claim 16, wherein the three actuators comprise three drive motors for selectively applying a tensile force on three of the four drive cables.

19. The system of claim 16, wherein each of the fingers comprises first, second, and third link members, the first link member being mounted to the palm element for rotation about first and second orthogonal axes, the second link member being pivotally mounted to an end of the first link member distal to the palm element, and the third link member being pivotally mounted to an end of the second link member distal to the first link member.

20. The system of claim 19, wherein a pair of the drive cables are attached to the second digit member and a pair of the drive cables are attached to the first digit link member to allow the actuators to independently move the first link member about the first and second axes and also to independently move the second link member relative to the first link member.

21. A robotic hand, comprising:
at least one finger assembly;
for each of the finger assemblies included in the robotic hand, a drive assembly selectively applying tension to four elongated and flexible tension elements;
an articulated wrist positioned between the finger assemblies and the drive assembly of each of the finger assemblies; and
cable conduits extending through the articulated wrist,
wherein each of the tension elements extends through one of the cable conduits,
wherein each of the finger assemblies comprises a set of links actuated by the tension elements,
wherein the links are interconnected with pivotal joints to have motion with three degrees-of-freedom, and
wherein the finger assembly further comprises a set of pulleys supported on the links to support and guide the tension elements in the finger assembly, the tension elements extending only partially about any one of the pulleys, whereby the finger assembly provides n+1 actuation with non-helical wrapping of the tension elements.

22. The robotic hand of claim 21, wherein at least a portion of the pulleys are single groove pulleys without helical wrappings and wherein the tension elements each comprise a cable.

23. The robotic hand of claim 22, wherein each of the cables wraps around less than half of the circumference of any of the pulleys.

24. The robotic hand of claim 21, wherein the set of links comprises a first digit link, a second digit link, and a third digit link, the third digit link being pivotally mounted to the second digit link and the second digit link being pivotally mounted to the first digit link, and wherein the first and second digit links are independently operable by the drive assembly applying tension to the tension elements.

25. A robotic hand, comprising:
at least one finger assembly; and
for each of the finger assemblies included in the robotic hand, a drive assembly selectively applying tension to four elongated and flexible tension elements;
wherein each of the finger assemblies comprises a set of links actuated by the tension elements,
wherein the links are interconnected with pivotal joints to have motion with three degrees-of-freedom,
wherein the finger assembly further comprises a set of pulleys supported on the links to support and guide the tension elements in the finger assembly, the tension elements extending only partially about any one of the pulleys, whereby the finger assembly provides n+1 actuation with non-helical wrapping of the tension elements,
wherein the set of links comprises a first digit link, a second digit link, and a third digit link, the third digit link being pivotally mounted to the second digit link and the second digit link being pivotally mounted to the first digit link, the first and second digit links being independently operable by the drive assembly applying tension to the tension elements, and
wherein the finger assembly further comprises an additional link coupling the third digit link to the second digit link such that the third digit link is actuated by movement of the second digit link as a passive follower link.

26. The robotic hand of claim 25, wherein at least a portion of the pulleys are single groove pulleys without helical wrappings, wherein the tension elements each comprise a cable, and wherein each of the cables wraps around less than half of the circumference of any of the pulleys.

27. The robotic hand of claim 25, further comprising an articulated wrist positioned between the finger assemblies and the drive assembly of each of the finger assemblies and further comprising cable conduits extending through the articulated wrist and wherein each of the tension elements extends through one of the cable conduits.

28. A robotic hand, comprising:
at least one finger assembly;
for each of the finger assemblies included in the robotic hand, a drive assembly selectively applying tension to four elongated and flexible tension elements, wherein each the finger assemblies further comprises a palm plate, a base link member, and a first digit mounting link member,
wherein each of the finger assemblies comprises a set of links actuated by the tension elements,
wherein the links are interconnected with pivotal joints to have motion with three degrees-of-freedom,
wherein the finger assembly further comprises a set of pulleys supported on the links to support and guide the tension elements in the finger assembly, the tension elements extending only partially about any one of the pulleys, whereby the finger assembly provides n+1 actuation with non-helical wrapping of the tension elements,
wherein the set of links comprises a first digit link, a second digit link, and a third digit link, the third digit link being pivotally mounted to the second digit link and the second digit link being pivotally mounted to the first digit link, and the first and second digit links being independently operable by the drive assembly applying tension to the tension elements,
wherein the base link member is rigidly attached to the palm plate to support the finger assembly,
wherein the first digit mounting link member is pivotally mounted to the base link member for pivoting about a first axis, and
wherein the first digit link is pivotally coupled to the first digit mounting link member for pivoting about a second axis transverse to the first axis.

29. The robotic hand of claim 28, wherein at least a portion of the pulleys are single groove pulleys without helical wrappings, wherein the tension elements each comprise a cable, and wherein each of the cables wraps around less than half of the circumference of any of the pulleys.

30. The robotic hand of claim 28, wherein a range of motion for the first digit mounting link member relative to the base link member is less than about 40 degrees to define a side-to-side movement of the first digit link and wherein a range of motion of the first digit link relative to the first digit mounting link member is less than about 15 degrees rotation about the second axis in a counterclockwise direction relative to a plane extending through the second axis and in a clockwise direction relative to the plane extending through the second axis is in the range of about 75 to 100 degrees.

31. The robotic hand of claim 28, further comprising:
an articulated wrist positioned between the finger assemblies and the drive assembly of each of the finger assemblies; and
cable conduits extending through the articulated wrist, wherein each of the tension elements extends through one of the cable conduits.

32. A robotic hand, comprising:
at least one finger assembly; and
for each of the finger assemblies included in the robotic hand, a drive assembly selectively applying tension to four elongated and flexible tension elements;
wherein each of the finger assemblies comprises a set of links actuated by the tension elements;
wherein the links are interconnected with pivotal joints to have motion with three degrees-of-freedom; and
wherein the finger assembly further comprises a set of pulleys supported on the links to support and guide the tension elements in the finger assembly, the tension elements extending only partially about any one of the pulleys, whereby the finger assembly provides n+1 actuation with non-helical wrapping of the tension elements, and
wherein the set of links comprises a first digit link, a second digit link, and a third digit link, the third digit link being pivotally mounted to the second digit link and the second digit link being pivotally mounted to the first digit link, and the first and second digit links being independently operable by the drive assembly applying tension to the tension elements,
wherein first and second ones of the tension elements terminate on the second digit link, and
wherein third and fourth ones of the tension elements terminate on the first digit link.

33. The robotic hand of claim 32, wherein at least a portion of the pulleys are single groove pulleys without helical wrappings, wherein the tension elements each comprise a cable, and wherein each of the cables wraps around less than half of the circumference of any of the pulleys.

34. The robotic hand of claim 32, further comprising:
an articulated wrist positioned between the finger assemblies and the drive assembly of each of the finger assemblies; and
cable conduits extending through the articulated wrist, wherein each of the tension elements extends through one of the cable conduits.

* * * * *